(12) United States Patent
Jenkins et al.

(10) Patent No.: US 6,201,132 B1
(45) Date of Patent: Mar. 13, 2001

(54) INHIBITORS OF DP-MEDIATED PROCESSES, COMPOSITIONS, AND THERAPEUTIC METHODS THEREOF

(75) Inventors: Paul D. Jenkins, Romsey; D. Michael Jones, Nr. Romsey; Michael Szelke, Romsey, all of (GB)

(73) Assignee: Ferring B.V., Hoofdorp (NL)

( * ) Notice: Subject to any disclaimer, the term of this patent is extended or adjusted under 35 U.S.C. 154(b) by 0 days.

(21) Appl. No.: 09/295,453

(22) Filed: Apr. 21, 1999

Related U.S. Application Data

(62) Division of application No. 08/647,887, filed as application No. PCT/GB94/00265 on Nov. 30, 1994, now Pat. No. 5,939,560.

(30) Foreign Application Priority Data

Dec. 3, 1993 (GB) .................................................. 93 24803
Dec. 6, 1993 (GB) .................................................. 93 24981

(51) Int. Cl.$^7$ ........................................................ C07K 5/06
(52) U.S. Cl. ............................. 548/535; 514/19; 548/400; 562/573
(58) Field of Search .............................. 514/19; 548/400, 548/535

(56) References Cited

U.S. PATENT DOCUMENTS 5,200,412     4/1993   Whittaker et al. .................. 514/293

FOREIGN PATENT DOCUMENTS

1221238 * 2/1971 (GB) .

91/16339 * 10/1991 (WO) .
93/08259 * 4/1993 (WO) .

OTHER PUBLICATIONS

Derwent Abstract of DD 296075 A, 1992.*
Derwent Abstract of DD 158109 A, 1983.*
Schon(Biol. Chem. Moppe–Seyler 372, 305), 1991.*
Demuth FEBS 320, 23–27, 1993.*
Patent Abstracts of Japan, 1(120) C77, 1977.*
Lotti Eur. J. Pharmacol. 162, 273, 1989.*

* cited by examiner

Primary Examiner—Christopher S. F. Low
Assistant Examiner—David Lukton
(74) Attorney, Agent, or Firm—Foley & Lardner

(57) ABSTRACT

Compounds selected from those of general formula

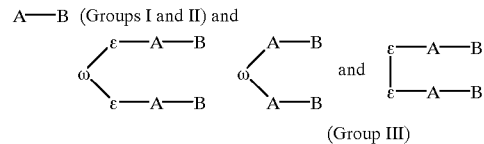

where B is

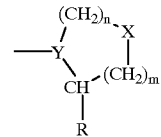

and A is selected from specified aminoacyl compounds are inhibitors of DP-IV mediated processes.

4 Claims, No Drawings

INHIBITORS OF DP-MEDIATED PROCESSES, COMPOSITIONS, AND THERAPEUTIC METHODS THEREOF

This application is a divisional of application Ser. No. 08/647,887, filed Aug. 27, 1996 now U.S. Pat. No. 5,939,560, which is a national stage of PCT/GB94/0265, filed Nov. 30. 1994.

BACKGROUND

DP-IV (EC 3.4.14.5) is a membrane-bound serine protease first identified in rat kidney by its ability to cleave dipeptides from the N-terminus of certain peptides (Hopsu-Havu, V. K. and Glenner, G. G., Histochemie, 1966, 2, 197). The dipeptides must be of the type X-Pro or X-Ala where X=any amino acid X-Proline is more efficiently cleaved than X-Ala.

DP-IV is widely distributed in mammalian tissues and is found in great abundance in the kidney, intestinal epithelium and placenta (Yaron, A. and Naider, F., Critical Reviews in Biochem. Mol. Biol. 1993, 28 (1), 31). In the human immune system the enzyme is expressed almost exclusively by activated T-lymphocytes of the $CD4^+$ type where the enzyme has been shown to be synonymous with the cell-surface antigen CD26.

The exact role of DP-IV in human physiology is not completely understood but recent research has shown that the enzyme clearly has a major role in human physiology and pathophysiology, eg.

(a) The immune response: DP-IV expression is increased in T-cells upon mitogenic or antigenic stimulation (Mattem, T. et al., Scand. J. Immunol. 1991, 33, 737). It has been reported that inhibitors of DP-IY and antibodies to DP-IV suppress the proliferation of mitogen- and antigen-stimulated T-cells in a dose-dependant manner (Schön, E. et al., Biol. Chem. Hoppe-Seyler, 1991, 372, 305 and refs. within).

Various other functions of T-lymphocytes such as cytokine production, IL-2 mediated cell proliferation and B-cell helper activity have been shown to be dependant on DP-IV activity (Schoin, E. et al., Scand. J. Immunol. 1989, 29, 127). Recently, DP-W inhibitors based on boroproline where reported (Flentke, G. R. et al., Proc. Nat. Acad. Sci. USA, 1991, 88, 1556) which, although unstable, were effective in inhibiting antigen-induced lymphocyte proliferation and IL-2 production in murine $CD4^+$ T-helper cells. Such boronic acid inhibitors have been shown to have an effect in vivo in mice causing suppression of antibody production induced by immune challenge (Kubota, T. et al., Clin. Exp. Immunol. 1992, 89 192). Other recent papers also provide evidence for the involvement of DP-IV in the immune response (eg. Tanaka, T. et al., Proc. Natl. Acad. Sci. N.Y., 1993, 9, 4586; Hegen, M. et al., Cell Immun. 1993, 146, 249; Subramanyan, M. et al., J. Immunol. 1993, 150, 2544).

The importance of DP-IV is attributed by some investigators to its cell-surface association with the trans-membrane phosphatase CD45 (Torimoto, Y. et al., J. Immunol. 1991, 147, 2514). The CD45 - DP-IV association is possibly disrupted by DP-IV inhibitors or non-active site ligands. CD45 is known to be an integral component of T-cell signaling.

(b) Recently, a press release from the Pasteur Institute in Paris (and subsequently a presentation by A. G. Hovanessian at the 8th Cent. Gardes Meeting, Paris, 25–27th October 1993) reported that DP-IV was essential for the penetration and infectivity of HIV-1 and HIV-2 viruses in $CD4^+$ T-cells. The French group claimed that DP-IV interacted with and may have cleaved the V3 loop of the gp120 envelope glyco-protein of the virus. They also reported that inhibitors or antibodies to DP-IV successfully prevented entry of the virus into cells. It was known previously that there is a selective decrease of CD26 expression in T-cells from HIV-1 infected individuals (Valle-Blazquez, M et al., J. Immunol. 1992, 149, 3073), and that HIV-1 Tat protein binds to DP-IV (Subramanyam, M. et al., J. Immunol. 1993, 150, 2544).

(c) It has been shown recently that lung endothelial DP-IV is an adhesion molecule for lung-metastatic rat breast and prostate carcinoma cells (Johnson, R. C. et al., J. Cell. Biol. 1993, 121, 1423). DP-IV is known to bind to fibronectin and some metastatic tumour cells are known to carry large amounts of fibronectin on their surface.

(d) DP-IV has been shown to associate with the enzyme adenosine deaminase (ADA) on the surface of T-cells (Kameoka, J. et al., Science, 193, 26 466). ADA deficiency causes severe combined immunodeficiency disease (SCID) in humans This ADA-CD26 interaction may provide clues to the pathophysiology of SCID.

(e) High levels of DP-IV expression have been found in human skin fibroblast cells from patients with psoriasis, rheumatoid arthritis (RA) and lichen planus (Raynaud, F. et al., J. Cell. Physiol. 1992, 151, 378).

(f) High DP-IV activity has been found in tissue homogenates from patients with benign prostate hypertrophy and in prostatosomes. These are prostate derived organelles important for the enhancement of sperm forward motility (Vanhoof, G. et al., Eur. J. Clin. Chem. Clin. Biochem. 1992, 30, 333).

(g) DP-IV has been shown to be responsible for the degradation and inactivation of circulating peptides with penultimate proline or alanine at the N-terminus, eg. substance P, growth hormone releasing factor and members of the glucagon/vasoactive intestinal peptide family (Menthein, R. et al., Eur. J. Biochem. 1993, 214, 829).

(h) Raised levels of DP-IV have been observed in the gingiva of patents with periodontitis (Cox, S. W. et al., Arch. Oral. Biol. 1992, 37, 167).

(i) There are also a number of other reports of raised (or sometimes lowered) levels of DP-IV in various pathological conditions.

It follows from the above that potent inhibitors of DP-IV may be useful as drugs for the treatment of human disease. Such inhibitors could be useful as:

(a) Immunosuppressants, eg. in organ transplantation; cytoline release suppressants eg. in various autoimmune diseases such as inflammatory bowel disease, multiple sclerosis, RA.

(b) Drugs for the prevention of HIV entry into T-cells and therefore useful in the prophylaxis and treatment of AIDS.

(c) Drugs for the prevention of metastases, particularly of breast and prostate tumours to the lungs.

(d) Agents to treat dermatological diseases, eg. psoriasis, lichen planus.

(e) Drugs to suppress sperm motility and therefore act as male contraceptive agents.

(f) Agents beneficial in benign prostate hypertrophy.
Inhibitors of DP-IV

The only competitive inhibitors of DP-IV enzyme activity reported so far are the unstable boronic acids (t½ 30–90 min at pH 7) mentioned above. (Bachovchin et al, WO 91/16339, October 1991) having $K_i$ values in the nanomolar range for DP-IV, and simple amino-acid pyrrolidides or thiazolides (Neubert et al., DD 296 075 A5, November 1991) which have only modest potency ($K_i$>0.1 $\mu$M). Amino-acyl proline aldehydes claimed in the same German patent cannot be synthesised due to a facile intramolecular condensation of the N-terminal amino group with the aldehyde function.

We now disclose highly potent competitive inhibitors of DP-IV (with $K_i$ values in the $10^{-6}$–$10^{-10}$ range) which are also chemically stable (t½>24 h). They fall into three broad groups of compounds (Groups I, II and III).

GROUP I

These are molecules designed to bind tightly in the active site of DP-IY and to inhibit its proteolytic activity without interfering with attachment of any accessory ligands which may bind to the surface of DP-IV (i.e. not at its active site). Such Group I compounds could be useful as immunosuppressants; anti-HIV infectivity agents; agents to suppress release of certain cytokines (eg. IL-2, IL-6, γ-INF) from activated T-cells. The boronic acids and pyrolidides referred to earlier also fall into this category.

GROUP II

These are evolved from Group I compounds; however they contain long-chain extensions to the side-chains of the amino-acid defined as A in the general structure. The resulting compounds bind tightly to the active-site of DP-IV but the long-chain extensions protrude from the enzyme active site and serve to prevent the attachment of any other ligand which may bind to the surface of DP-IV. Such compounds could have the same uses as Group I compounds but in addition could block the interaction of DP-IY with (i) CD45 (ii) the gp 120 V3 loop of HIV-1 (iii) tumour cell surface fibronectin (iv) any other ligand important for T-cell activation, virus entry into T-cells or tumour cell adhesion.

GROUP III

This group comprises novel dimers in which two active-site directed inhibitors of DP-IV are linked via the side-chains of their amino-acid residues designated A in the general structure by a long chain. Such dimers can inhibit two molecules of DP-IV concurrently and also prevent accessory ligands binding to the surface of DP-IV. These dimers would have the same uses as Group II compounds but may be more effective.

The invention provides inhibitors of DP-IV mediated processes, the inhibitors being of general formula:

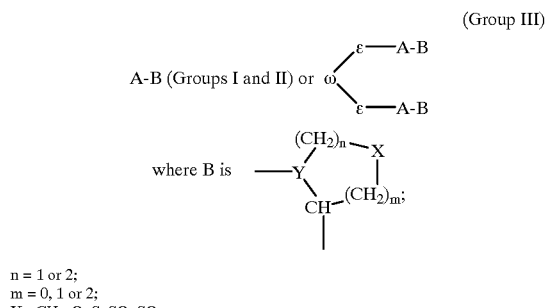

n = 1 or 2;
m = 0, 1 or 2;
X= CH$_2$, O, S, SO, SO$_2$,
NH or NR$_1$ where R$_1$ = lower alkyl (C$_1$ to C$_6$);

A is attached to Y;
—Y=—N, —CH or =C (when the —CO group of A is replaced with CH= or CF=);

R=H, CN, CHO, B(OH)$_2$, C≡C—R$_7$, or CH=N—R$_8$;
R$_7$=H, F, lower alkyl (C$_1$ to C$_6$), CN, NO$_2$, OR$_9$, CO$_2$R$_9$ or COR$_9$;
R$_8$=Ph, OH, OR$_9$, OCOR$_9$, or OBn;
R$_9$=lower alkyl (C$_1$–C$_6$); and either ω or both ε's may be absent.

The structure of A is dependent on the nature of R in moiety B and on the nature of the group to which the resulting compound belongs.

Group I Compounds
(a) R=H
A is an α-amino-acyl group derived from an α-amino-acid bearing a cycloaliphatic side-chain (e.g. C$_4$ to C$_{10}$, mono or bicyclic) whose ring may contain one or more heteroatoms e.g. L-cyclohexylglycine, L-cyclopentylglycine, L-decahydronaphthylglycine, L-piperidylglycine;
or
A is a β-amino-acyl group of general formula

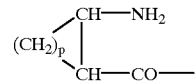

where p=1–6 and the ring may also contain one or more heteroatoms replacing CH$_2$ unit(s).

Both α and β-amino acyl groups in (a) above may contain unsaturation in their rings e.g.

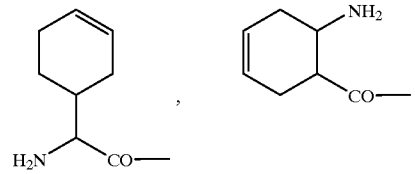

and also may contain one or more heteroatoms.
(b) R=CN; C≡C—R$_7$ or CH=N—R$_8$
A is as defined in (a) above but in addition may be derived from any L-α-amino acid bearing a lipophilic side-chain, eg. Ile.
(c) R=CHO or B(OH)$_2$
A is a β-amino-acyl group as defined in (a) above. The resulting A–B compounds are stable, unlike α-aminoacyl derivatives of the same type which undergo a facile intramolecular cyclisation. In compounds (c) B(OH)$_2$ may be present as a boronate ester eg.

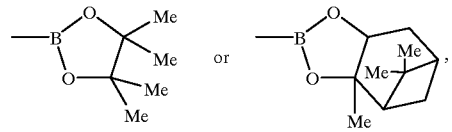

these being labile in water giving the free boronic acids.
Group II Compounds
Where R=H, CN, C≡C—R$_7$ or CH=N—R$_8$, A is an α-amino acid derivative whose side-chain carries a functional group which is derivatised to produce a long chain terminating in various groups R$_3$. A may be of the following three types of structure:

(i)

$$H_2N-\underset{\underset{|}{CO}}{\overset{}{C}}-(CH_2)-{}^aCO-D \quad \text{or} \quad H_2N-\underset{\underset{|}{CO}}{\overset{}{C}}-(CH_2)_a-SO_2-D^1$$

where
a=1–5; D=G—$(CH_2)_b(R_4)_q$—$R_3$; G=O, NH, or NMe;
b=0–12; q=0–5;
$D^1$=D with G≠O;
$R_4$=Z—NH—$(CH_2)_c$— or NH—Z—$(CH_2)_c$— where c=1–12 and Z=CO, $CH_2$ or $SO_2$; and
$R_3$=$CO_2H$ or ester [e.g. any lower alkyl, fluoroalkyl or cycloalkyl ($C_1$ to $C_8$), or aromatic or heteroaromatic (5 or 6membered rings, mono- or bicylic) ester] thereof; $CONH_2$; $CONHNH_2$; $CONR_5R_6$; $CONHNR_5R_6$; $PO_3H$ (or ester thereof e.g. as defined under $CO_2H$); $SO_3H$; $SO_2NH_2$; $SO_2NR_5R_6$; OH; $OR_5$; aryl or heteroaryl (e.g. 5 or 6membered rings, monocyclic or bicyclic) [including substituted aryl or heteroaryl with substituents preferably chosen from F, Cl, I, Br, OH, $OR_5$, $NO_2$, $SO_3H$, $SO_2NH_2$, $SO_2NR_5R_6$, $NH_2$, $NR_5R_6$, $CO_2R_5$, $CF_3$, CN, $CONH_2$, $CONR_5R_6$, $NHCO_2R_5$, $CH(:NR_5)NR_5R_6$, NH—$CH(:NR_5)NR_5R_6$ and $R_5$]; $NH_2$; $NR_5R_6$; $NHCO_2R_5$; $NHSO_2NR_5R_6$; $NHCOR_5$; NH—$SO_2R_5$; NH—$CH(:NR_5)NR_5R_6$; $NHCONR_5R_6$; sugar (which may be attached via an ether or a glycosidic bond); CO-aminosugar (attached via the —$NH_2$) eg. glucosamine or galactosamine; NHCO-aminosugar; or NHCS-aminosugar.

In the above definition of $R_3$ "sugar" refers to any carbohydrate or oligosaccharide, and $R_5$ and $R_6$ are independently selected from H and alkyl, fluoroallyl and cycloalkyl groups (of up to 8 atoms), aryl, heteroaryl and alkylheteroaryl groups (of up to 11 atoms) or $R_5$ and $R_6$ together comprise a chain and ($C_3$ to $C_8$).

(ii)

$$H_2N-\underset{\underset{|}{CO}}{\overset{}{C}}-(CH_2)_aNR^1E \quad \text{or} \quad H_2N-\underset{\underset{|}{CO}}{\overset{}{C}}-\langle\text{piperidine}\rangle-N-E$$

where $R^1$=H, Me; the ring may also contain more heteroatoms;
E=J—$(CH_2)_b$—$(R_4)_q$—$R_3$; J=CO, $CH_2$ or $SO_2$; and a, b, q, $R_3$ and $R_4$ as defined under (i)

(iii)

$$H_2N-\underset{\underset{|}{CO}}{\overset{}{C}}\langle{R^2 \atop OL}\rangle \quad \text{or} \quad H_2N-\underset{\underset{|}{CO}}{\overset{}{C}}-\langle\text{cyclohexyl}\rangle-OL$$

where $R^2$=H or Me; the ring may also contain one or more heteroatoms;
L=$(CH_2)_d$—$[CO]_r$—$(CH_2)_b$—$(R_4)_1$—$R_3$ or $(CH_2)_e$—$NR^1$—$(CH_2)_b$—$(R_4)_q$—$R_3$; r=0 or 1; d=0–4; e=2–4; and b, q, $R_3$ and $R_4$ as defined under (i).

Group III

Group III compounds are defined by the general formula:

$$\omega\langle{\epsilon-A-B \atop \epsilon-A-B}\rangle$$

where ω=$CH_2$, O, NH, CO, S, $SO_2$, Ph or NMe and, independently, ε=$CH_2$, O, NH, CO, S, $SO_2$, Ph or NMe.

These compounds are symmetrical dimers. They may have any B structure as defined previously. A may be chosen from any group II structure [(i), (ii) or (iii)], but in this case he terminal group $R_3$ in each A residue is deleted and replaced with a shared symmetrical group [ε—ωε] which connects the two halves of the dimer; ω may be absent, in which case both ε's are joined together to constitute the chain linking the two A–B moieties; alternatively both ε's may be absent in which case to solely joins the two A–B moieties.

The stricture of ε—ω—ε must of course be chemically feasible eg. NH—CO—NH, CO—NH—CO—, $SO_2$—NMe—$SO_2$; it will be obvious to those skilled in the art which structures are not feasible, eg. —NH—NH—NH—. A specific possible example is shown in Table 7.

In such compounds as described under Groups II and III certain —$CH_2$— groups present in the long chains could be replaced with known bioisosteres eg. —O— without affecting inhibitory or binding activity towards DP-IV. Also such groupings as —$CONHCH_2CH_2NHCO$ if they occur could be replaced by eg.

$$-CO-N\langle\text{piperazine}\rangle N-CO-.$$

Further, for compounds in Groups I, II and III any amide bond connecting A and B or any amide in the side-chains of A (in Groups II and E) may be replaced by known bioisosteres of amides eg.

—CO—N⟨ replaced by —CO—C⟨ ; CF=C⟨ ;

—$CH_2$—N⟨ ; CH=C⟨ ; —CS—N⟨ .

See Table 8 for examples of such replacements.

Biochemistry

All compounds were tested in vitro against pure human DP-IV (purchased from M & E, Copenhagen, Denmark). Inhibition of DP-IV was determined using the fluorescent substrate Ala—Pro—AFC ($K_m$ 0.8 μM) at three concentrations for each inhibitor. A typical assay (total volume 0.4 ml) comprised sodium Hepes 83.3 mM, EDTA 1.67 mM, BSA 1.5 mg ml$^{-1}$ pH 7.8, DP-IV 25 μU ml$^{-1}$, inhibitor (in 10 mM acetate pH 4.0). The reaction was started by the addition of substrate and readings taken every 30 s for 7.5 min, excitation at 395 nm, emission 450 nm. $K_i$ values were determined using Dixon plots.

Chemistry

152 Examples of compounds synthesised are shown in Tables 1–8 followed by schemes and experimental details for the preparation of different structural types. All final products were characterised by FAB mass spectrometry and purity assessed by reverse phase hplc; all intermediates were characterised by ¹H NMR.

Table 9 shows selected $K_i$ values against DP—IV determined for inhibitors of different structural types.

TABLE 1

Examples of Group I (a)

| No. | A | X | R | n | Formula | Calculated Mol. Wt. | FAB Mass spec. [M + H]⁺ |
|---|---|---|---|---|---|---|---|
| 1 | (cyclopentyl-CH(NH₂)-C(=O)-) | CH₂ | H | 1 | $C_{11}H_{20}N_2O$ | 196.2 | 197.2 |
| 2 | (cyclohexyl-CH(NH₂)-C(=O)-) | CH₂ | H | 1 | $C_{12}H_{22}N_2O$ | 210.2 | 211.2 |
| 3 | (tert-butyl-CH(NH₂)-C(=O)-) | CH₂ | H | 1 | $C_{10}H_{20}N_2O$ | 184.2 | 185.2 |
| 4 | (cyclohexenyl-CH(NH₂)-C(=O)-) | CH₂ | H | 1 | $C_{12}H_{20}N_2O$ | 208.2 | 209.2 |
| 5 cis | (2-aminocyclohexyl-C(=O)CH₃) | CH₂ | H | 1 | $C_{11}H_{20}N_2O$ | 196.1 | 197.2 |
| 6 trans | (2-aminocyclohexyl-C(=O)CH₃) | CH₂ | H | 1 | $C_{11}H_{20}N_2O$ | 196.1 | 197.2 |
| 7 trans | (2-aminocyclohexenyl-C(=O)CH₃) | CH₂ | H | 1 | $C_{11}H_{18}N_2O$ | 194.1 | 195.2 |

TABLE 1-continued

Examples of Group I (a)

| No. | A | X | R | n | Formula | Calculated Mol. Wt. | FAB Mass spec. [M + H]$^+$ |
|---|---|---|---|---|---|---|---|
| 8 trans | (2-aminocyclopentyl methyl ketone) | $CH_2$ | H | 1 | $C_{10}H_{18}N_2O$ | 182.1 | 183.2 |
| 9 | (2-aminophenyl methyl ketone) | $CH_2$ | H | 1 | $C_{11}H_{14}N_2O$ | 190.1 | 191.2 |
| 10 trans | (2-aminocyclooctyl methyl ketone) | $CH_2$ | H | 1 | $C_{13}H_{24}N_2O$ | 224.2 | 225.2 |

TABLE 2

Examples of Group I (b)

| No. | A | X | n | R$^1$ | R | Formula | Calculated Mol. Wt. | FAB Mass spec. [M + H]$^+$ |
|---|---|---|---|---|---|---|---|---|
| 11 | H-Ile | $CH_2$ | 1 | H | CN | $C_{11}H_{19}N_3O$ | 209.3 | 210.2 |
| 12 | H-Lys(Z) | $CH_2$ | 1 | H | CN | $C_{19}H_{26}N_4O_3$ | 358.2 | 359.2 |
| 13 | H-Pro | $CH_2$ | 1 | H | CN | $C_{10}H_{15}N_3O$ | 193.1 | 194.1 |
| 14 | (thiazolidine-4-carbonyl) | $CH_2$ | 1 | H | CN | $C_9H_{13}N_3OS$ | 211.1 | 212.2 |
| 15 | (thiazolidine-2-carbonyl) | $CH_2$ | 1 | H | CN | $C_9H_{13}N_3OS$ | 211.1 | 212.2 |
| 16 | (cyclohexyl-glycyl) | $CH_2$ | 1 | H | CN | $C_{13}H_{21}N_3O$ | 235.2 | 236.3 |

TABLE 2-continued

Examples of Group I (b)

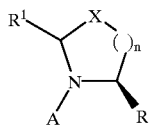

| No. | A | X | n | R¹ | R | Formula | Calculated Mol. Wt. | FAB Mass spec. [M + H]⁺ |
|---|---|---|---|---|---|---|---|---|
| 17 | (cyclohexyl-CH(NH₂)-C(O)-) | $CH_2$ | 1 | H | CN | $C_{12}H_{19}N_3O$ | 221.2 | 222.2 |
| 18 | (tBu-CH(NH₂)-C(O)-) | $CH_2$ | 1 | H | CN | $C_{11}H_{19}N_3O$ | 209.2 | 210.2 |
| 19 | H-Ile | S | 1 | H | CN | $C_{10}H_{17}N_3OS$ | 227.1 | 228.1 |
| 20 | H-Ile | S | 1 | CN | H | $C_{10}H_{17}N_3OS$ | 227.1 | 228.1 |
| 21 | (cyclohexyl-CH(NH₂)-C(O)-) | S | 1 | H | CN | $C_{12}H_{19}N_3OS$ | 253.1 | 254.1 |
| 22 | H-Lys(Z) | S | 1 | H | CN | $C_{18}H_{24}N_4O_3S$ | 376.2 | 3.2 |
| 23 | (cyclopentyl-CH(NH₂)-C(O)-) | S | 1 | H | CN | $C_{11}H_{17}N_3OS$ | 239.1 | 240.2 |
| 24 | H-Ile | O | 1 | H | CN | $C_{10}H_{17}N_3O_2$ | 211.1 | 212.2 |
| 25 | H-Ile | $CH_2$ | 2 | H | CN | $C_{12}H_{21}N_3O$ | 223.2 | 224.2 |
| 26 | H-Ile | S | 2 | H | CN | $C_{11}H_{19}N_3OS$ | 241.1 | 242.1 |
| 27 | H-Ile | $SO_2$ | 1 | H | CN | $C_{10}H_{17}N_3O_3S$ | 259.1 | 260.1 |
| 28 | H-Ile | S⁺···O⁻ | 1 | H | CN | $C_{10}H_{17}N_3O_2S$ | 243.1 | 244.1 |
| 29 | H-Ile | S⁺◀O⁻ | 1 | H | CN | $C_{10}H_{17}N_3O_2S$ | 243.1 | 244.2 |
| 30 | (trans-2-aminocyclohexyl-C(O)-) | $CH_2$ | 1 | H | CN | $C_{12}H_{19}N_3O$ | 221.2 | 222.2 |

TABLE 2-continued
Examples of Group I (b)
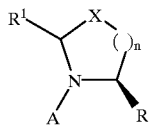
| No. | A | X | n | R¹ | R | Formula | Calculated Mol. Wt. | FAB Mass spec. [M + H]⁺ |
|---|---|---|---|---|---|---|---|---|
| 31 | (2-aminocyclohexyl, trans) | $CH_2$ | 1 | H | CN | $C_{12}H_{19}N_3O$ | 221.2 | 222.2 |
| 32 | (2-aminocyclopentyl) | $CH_2$ | 1 | H | CN | $C_{11}H_{17}N_3O$ | 207.2 | 208.2 |
| 33 | (2-aminocyclopentyl) | $CH_2$ | 1 | H | CN | $C_{11}H_{17}N_3O$ | 207.2 | 208.2 |
| 34 | (2-aminocyclohexenyl) | $CH_2$ | 1 | H | CN | $C_{12}H_{17}N_3O$ | 219.1 | 220.1 |
| 35 | (2-aminocyclohexenyl) | $CH_2$ | 1 | H | CN | $C_{12}H_{17}N_3O$ | 219.1 | 220.1 |
| 36 | (2-aminocyclohexyl) | $CH_2$ | 1 | H | CN | $C_{12}H_{19}N_3O$ | 221.2 | 222.2 |
| 37 | (2-aminocyclohexenyl) | $CH_2$ | 1 | H | CN | $C_{12}H_{17}N_3O$ | 219.1 | 220.1 |

TABLE 3

Example of Group I (c)

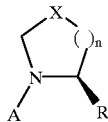

| No. | A | X | R | n | Formula | Calculated Mol. Wt. | FAB Mass spec. [M + H]+ |
|---|---|---|---|---|---|---|---|
| 38 | (cyclohexane with NH2 and C(=O)-) | CH$_2$ | CHO | 1 | C$_{12}$H$_{20}$N$_2$O$_2$ | 224.2 | 225.2 |
| 39 | (cyclopentane with H$_2$N and C(=O)-) | CH$_2$ | CHO | 1 | C$_{11}$H$_{18}$N$_2$O$_2$ | 210.2 | 211.2 |
| 40 | (cyclopentane with H$_2$N and C(=O)-) | CH$_2$ | CHO | 1 | C$_{11}$H$_{18}$N$_2$O$_2$ | 210.2 | 211.2 |
| 41 | (cyclopentane with H$_2$N and C(=O)-) | CH$_2$ | B* | 1 | C$_{20}$H$_{33}$BN$_2$O$_3$ | 360.3 | 361.3 |
| 42 | (cyclohexane with NH$_2$ and C(=O)-) | CH$_2$ | B* | 1 | C$_{21}$H$_{35}$BN$_2$O$_3$ | 374.3 | 375.1 |
| 43 | (cyclohexane with NH$_2$ and C(=O)-) | CH$_2$ | B* | 1 | C$_{21}$H$_{35}$BN$_2$O$_3$ | 374.3 | 375.1 |
| 44 | (cyclohexene with NH$_2$ and C(=O)-) | CH$_2$ | B* | 1 | C$_{21}$H$_{33}$BN$_2$O$_3$ | 372.3 | 373.3 |

TABLE 3-continued

Example of Group I (c)

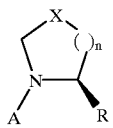

| No. | A | X | R | n | Formula | Calculated Mol. Wt. | FAB Mass spec. [M + H]+ |
|---|---|---|---|---|---|---|---|
| 45 | 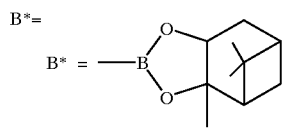 | $CH_2$ | B* | 1 | $C_{21}H_{33}BN_2O_3$ | 372.3 | 373.3 |

B* =

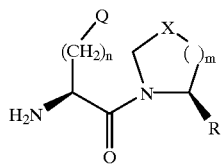

TABLE 4

Examples of Group II (i)

| No. | n | Q | X | m | R | Formula | Calculated Mol. Wt. | FAB Mass spec. [M + H]+ |
|---|---|---|---|---|---|---|---|---|
| 46 | 1 | —$CONHCH_2CO_2Bn$ | $CH_2$ | 1 | H | $C_{17}H_{23}N_3O_4$ | 333.2 | 334.2 |
| 47 | 1 | —$CONHCH_2CO_2H$ | $CH_2$ | 1 | H | $C_{10}H_{17}N_3O_4$ | 243.1 | 244.2 |
| 48 | 1 | —$CONH(CH_2)_3CO_2H$ | $CH_2$ | 1 | H | $C_{12}H_{21}N_3O_4$ | 271.2 | 272.2 |
| 49 | 1 | —$CONH(CH_2)_2CO_2Bn$ | $CH_2$ | 1 | H | $C_{18}H_{25}N_3O_4$ | 347.2 | 348.2 |
| 50 | 1 | —$CONH(CH_2)_2CO_2H$ | $CH_2$ | 1 | H | $C_{11}H_{19}N_3O_4$ | 257.1 | 258.2 |
| 51 | 1 | —$CONH(CH_2)_5CO_2Bn$ | $CH_2$ | 1 | H | $C_{21}H_{31}N_3O_4$ | 389.3 | 390.3 |
| 52 | 1 | —$CONH(CH_2)_5CO_2H$ | $CH_2$ | 1 | H | $C_{14}H_{25}N_3O_4$ | 299.2 | 300.2 |
| 53 | 1 | —$CONH(CH_2)_3CO_2Bn$ | $CH_2$ | 1 | H | $C_{19}H_{27}N_3O_4$ | 361.2 | 362.2 |
| 54 | 2 | —$CONHCH_2CO_2Bn$ | $CH_2$ | 1 | H | $C_{18}H_{25}N_3O_4$ | 347.2 | 348.2 |
| 55 | 2 | —$CONHCH_2CO_2H$ | $CH_2$ | 1 | H | $C_{11}H_{19}N_3O_4$ | 257.1 | 258.1 |
| 56 | 2 | —$CONH(CH_2)_2CO_2Bn$ | $CH_2$ | 1 | H | $C_{19}H_{27}N_3O_4$ | 361.2 | 362.3 |
| 57 | 2 | —$CONH(CH_2)_3CO_2Bn$ | $CH_2$ | 1 | H | $C_{20}H_{29}N_3O_4$ | 375.2 | 376.3 |
| 58 | 2 | —$CONH(CH_2)_3CO_2H$ | $CH_2$ | 1 | H | $C_{13}H_{23}N_3O_4$ | 285.2 | 286.2 |
| 59 | 2 | —$CONH(CH_2)_5CO_2Bn$ | $CH_2$ | 1 | H | $C_{22}H_{33}N_3O_4$ | 403.3 | 404.3 |
| 60 | 2 | —$CONH(CH_2)_5CO_2H$ | $CH_2$ | 1 | H | $C_{15}H_{27}N_3O_4$ | 313.2 | 314.2 |
| 61 | 2 | —$CONH(CH_2)_2CO_2H$ | $CH_2$ | 1 | H | $C_{12}H_{21}N_3O_4$ | 271.2 | 272.2 |
| 62 | 2 | —$CONH(CH_2)_7CO_2Bn$ | $CH_2$ | 1 | H | $C_{24}H_{37}N_3O_4$ | 432.3 | 432.4 |
| 63 | 2 | —$CONH(CH_2)_7CO_2H$ | $CH_2$ | 1 | H | $C_{17}H_{31}N_3O_4$ | 341.3 | 342.5 |
| 64 | 2 | —$CONH(CH_2)_7CONH—(CH_2)_3NHZ$ | $CH_2$ | 1 | H | $C_{28}H_{45}N_5O_5$ | 531.3 | 532.3 |
| 65 | 2 | —$CONH(CH_2)_6CONH—(CH_2)_5CO_2Bn$ | $CH_2$ | 1 | H | $C_{29}H_{46}N_4O_5$ | 530.4 | 531.2 |
| 66 | 2 | —$CONH(CH_2)_6CONH—(CH_2)_5CO_2H$ | $CH_2$ | 1 | H | $C_{22}H_{40}N_4O_5$ | 440.3 | 441.3 |
| 67 | 2 | —$CONH(CH_2)_7CONH—(CH_2)_3NH_2$ | $CH_2$ | 1 | H | $C_{20}H_{39}N_5O_3$ | 397.3 | 398.3 |
| 68 | 2 | —$CONH(CH_2)_{11}CO_2Bn$ | $CH_2$ | 1 | H | $C_{28}H_{45}N_3O_4$ | 487.3 | 488.4 |
| 69 | 2 | —$CONH(CH_2)_{11}CO_2H$ | $CH_2$ | 1 | H | $C_{21}H_{39}N_3O_4$ | 397.3 | 398.3 |
| 70 | 2 | —$CONH(CH_2)_6CO_2Bn$ | $CH_2$ | 1 | H | $C_{23}H_{35}N_3O_4$ | 417.3 | 418.3 |
| 71 | 2 | —$CONH(CH_2)_6CO_2H$ | $CH_2$ | 1 | H | $C_{16}H_{29}N_3O_4$ | 327.2 | 328.2 |
| 72 | 2 | —$CONH(CH_2)_5CONH—CH_2CF_3$ | $CH_2$ | 1 | H | $C_{17}H_{29}F_3N_4O_3$ | 394.2 | 395.3 |
| 73 | 2 | —$CONH(CH_2)_5CONH—CH_2(CF_2)_2CF_3$ | $CH_2$ | 1 | H | $C_{19}H_{29}F_7N_4O_3$ | 494.2 | 495.2 |
| 74 | 2 | —$CONH(CH_2)_5CONH—(CH_2)_6OH$ | $CH_2$ | 1 | H | $C_{21}H_{40}N_4O_4$ | 412.3 | 413.2 |
| 75 | 2 | —$CONH(CH_2)_5CONH—(CH_2)_3Ph$ | $CH_2$ | 1 | H | $C_{24}H_{38}N_4O_3$ | 430.3 | 431.2 |
| 76 | 2 | —$CONH(CH_2)_5CONH—(CH_2)_4Ph$ | $CH_2$ | 1 | H | $C_{25}H_{40}N_4O_3$ | 444.3 | 445.2 |

TABLE 4-continued

Examples of Group II (i)

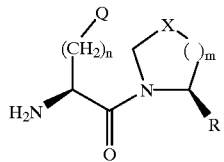

| No. | n | Q | X | m | R | Formula | Calculated Mol. Wt. | FAB Mass spec. [M + H]+ |
|---|---|---|---|---|---|---|---|---|
| 77 | 2 | —CONH(CH$_2$)$_5$CON-($^n$Bu)$_2$ | CH$_2$ | 1 | H | C$_{23}$H$_{44}$N$_4$O$_3$ | 424.3 | 425.3 |
| 78 | 2 | —CONH(CH$_2$)$_5$CON-($^n$Hx)$_2$ | CH$_2$ | 1 | H | C$_{27}$H$_{52}$N$_4$O$_3$ | 480.4 | 481.4 |
| 79 | 2 | —CONH(CH$_2$)$_5$CONH—CH$_2$Ph | CH$_2$ | 1 | H | C$_{22}$H$_{34}$N$_4$O$_3$ | 402.3 | 403.4 |
| 80 | 2 | —CONH(CH$_2$)$_4$CO$_2$Bn | CH$_2$ | 1 | H | C$_{21}$H$_{31}$N$_3$O$_4$ | 389.2 | 390.3 |
| 81 | 2 | —CONH(CH$_2$)$_4$CO$_2$H | CH$_2$ | 1 | H | C$_{14}$H$_{25}$N$_3$O$_4$ | 299.2 | 300.3 |
| 82 | 2 | —CONH(CH$_2$)$_5$CONH—CH$_2$CH$_3$ | CH$_2$ | 1 | H | C$_{17}$H$_{32}$N$_4$O$_3$ | 340.3 | 341.3 |
| 83 | 2 | —CONH(CH$_2$)$_6$OH | CH$_2$ | 1 | H | C$_{15}$H$_{29}$N$_3$O$_3$ | 299.2 | 300.3 |
| 84 | 2 | —CONH(CH$_2$)$_5$CO-1-Pip | CH$_2$ | 1 | H | C$_{20}$H$_{36}$N$_4$O$_3$ | 380.3 | 381.4 |
| 85 | 2 | —CONH(CH$_2$)$_5$CONH$_2$ | CH$_2$ | 1 | H | C$_{15}$H$_{28}$N$_4$O$_3$ | 312.2 | 313.3 |
| 86 | 2 | —CONH(CH$_2$)$_5$CONH—(CH$_2$)$_9$CH$_3$ | CH$_2$ | 1 | H | C$_{25}$H$_{48}$N$_4$O$_3$ | 452.4 | 453.5 |
| 87 | 2 | —CONH(CH$_2$)$_5$CONH—(CH$_2$)$_6$CH$_3$ | CH$_2$ | 1 | H | C$_{22}$H$_{42}$N$_4$O$_3$ | 410.3 | 411.4 |
| 88 | 2 | —CONH(CH$_2$)$_5$CONH—CH$_2$Ch | CH$_2$ | 1 | H | C$_{22}$H$_{40}$N$_4$O$_3$ | 408.3 | 409.4 |
| 89 | 2 | —CONH(CH$_2$)$_5$CONH—(CH$_2$)$_3$NHZ | CH$_2$ | 1 | H | C$_{26}$H$_{41}$N$_5$O$_5$ | 503.3 | 504.4 |
| 90 | 2 | —CONH(CH$_2$)$_5$CONH—(CH$_2$)$_3$NH$_2$ | CH$_2$ | 1 | H | C$_{18}$H$_{35}$N$_5$O$_3$ | 369.3 | 370.3 |
| 91 | 2 | —CONH(CH$_2$)$_5$CONH—(CH$_2$)$_3$—Gua | CH$_2$ | 1 | H | C$_{19}$H$_{37}$N$_7$O$_3$ | 411.3 | 412.4 |
| 92 | 2 | —CONH(CH$_2$)$_5$CONH—Ph(4-SO$_3$H) | CH$_2$ | 1 | H | C$_{21}$H$_{32}$N$_4$O$_6$S | 468.2 | 469.2 |
| 93 | 2 | —CONH(CH$_2$)$_5$CONH-4-Pip(1-Bn) | CH$_2$ | 1 | H | C$_{27}$H$_{43}$N$_5$O$_3$ | 485.3 | 486.3 |
| 94 | 2 | —CONH(CH$_2$)$_5$CONH-4-Pip | CH$_2$ | 1 | H | C$_{20}$H$_{37}$N$_5$O$_3$ | 395.3 | 396.3 |
| 95 | 2 | —CONH(CH$_2$)$_4$N(Z)—(CH$_2$)$_3$NHZ | CH$_2$ | 1 | H | C$_{32}$H$_{45}$N$_5$O$_6$ | 595.3 | 596.3 |
| 96 | 2 | —CONH(CH$_2$)$_4$NH—(CH$_2$)$_3$NH$_2$ | CH$_2$ | 1 | H | C$_{16}$H$_{35}$N$_5$O$_2$ | 327.2 | 328.2 |
| 97 | 2 | —CONH(CH$_2$)$_5$CO$_2$Bn | CH$_2$ | 1 | CN | C$_{23}$H$_{32}$N$_4$O$_4$ | 428.3 | 429.3 |
| 98 | 3 | —CONH(CH$_2$)$_6$CONH—(CH$_2$)$_5$CO$_2$Bn | CH$_2$ | 1 | H | C$_{30}$H$_{48}$N$_4$O$_5$ | 544.4 | 545.2 |
| 99 | 3 | —CONH(CH$_2$)$_6$CONH—(CH$_2$)$_5$CO$_2$H | CH$_2$ | 1 | H | C$_{23}$H$_{42}$N$_4$O$_5$ | 454.3 | 455.3 |
| 100 | 3 | —CONH(CH$_2$)$_5$CO$_2$Bn | CH$_2$ | 1 | H | C$_{23}$H$_{35}$N$_3$O$_4$ | 417.3 | 418.2 |
| 101 | 3 | —CONH(CH$_2$)$_5$CO$_2$H | CH$_2$ | 1 | H | C$_{16}$H$_{29}$N$_3$O$_4$ | 327.2 | 328.2 |
| 102 | 2 | —SO$_2$NH(CH$_2$)$_5$CO$_2$H | CH$_2$ | 1 | H | C$_{14}$H$_{27}$N$_3$O$_5$S | 349.2 | 350.2 |
| 103 | 2 | —CONH(CH$_2$)$_8$NH—G* | CH$_2$ | 1 | H | C$_{24}$H$_{45}$N$_5$O$_7$S | 547.4 | 548.5 |

G*=

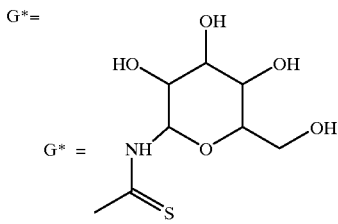

TABLE 5

Example of Group II (ii)

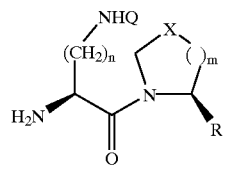

| No. | n | Q | X | m | R | Formula | Calculated Mol. Wt. | FAB Mass spec. [M + H]+ |
|---|---|---|---|---|---|---|---|---|
| 104 | 1 | —CO(CH$_2$)$_6$CO$_2$H | CH$_2$ | 1 | H | C$_{15}$H$_{27}$N$_3$O$_4$ | 313.2 | 314.3 |
| 105 | 1 | —CO(CH$_2$)$_6$CO$_2$Bn | CH$_2$ | 1 | H | C$_{22}$H$_{33}$N$_3$O$_4$ | 403.3 | 404.3 |
| 106 | 3 | —CO(CH$_2$)$_4$CO$_2$H | CH$_2$ | 1 | H | C$_{15}$H$_{27}$N$_3$O$_4$ | 313.2 | 314.3 |
| 107 | 3 | —CO(CH$_2$)$_4$CO$_2$Me | CH$_2$ | 1 | H | C$_{16}$H$_{29}$N$_3$O$_4$ | 327.2 | 328.3 |
| 108 | 4 | —CO(CH$_2$)$_5$NH$_2$ | CH$_2$ | 1 | H | C$_{16}$H$_{32}$N$_4$O$_2$ | 312.3 | 313.3 |

TABLE 5-continued

Example of Group II (ii)

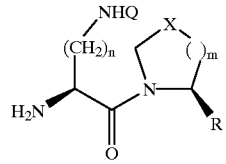

| No. | n | Q | X | m | R | Formula | Calculated Mol. Wt. | FAB Mass spec. [M + H]+ |
|---|---|---|---|---|---|---|---|---|
| 109 | 4 | —CO(CH$_2$)$_3$NH$_2$ | CH$_2$ | 1 | H | C$_{14}$H$_{28}$N$_4$O$_2$ | 284.2 | 285.2 |
| 110 | 4 | —CO(CH$_2$)$_3$NHSO$_2$Pfp | CH$_2$ | 1 | H | C$_{20}$H$_{27}$F$_5$N$_4$O$_4$S | 514.2 | 515.2 |
| 111 | 4 | —CO(CH$_2$)$_3$NHCOPfp | CH$_2$ | 1 | H | C$_{21}$H$_{27}$F$_5$N$_4$O$_3$ | 478.2 | 479.2 |
| 112 | 4 | —CO(CH$_2$)$_3$NHSO$_2$—CH$_2$CF$_3$ | CH$_2$ | 1 | H | C$_{16}$H$_{29}$F$_3$N$_4$O$_4$S | 430.2 | 431.3 |
| 113 | 4 | —CO(CH$_2$)$_{11}$NHCO—(CH$_2$)$_6$NHZ | CH$_2$ | 1 | H | C$_{37}$H$_{63}$N$_5$O$_5$ | 657.5 | 658.6 |
| 114 | 4 | —CO(CH$_2$)$_{11}$NH—CO(CH$_2$)$_6$NH$_2$ | CH$_2$ | 1 | H | C$_{29}$H$_{57}$N$_5$O$_3$ | 523.4 | 524.4 |
| 115 | 4 | —CO(CH$_2$)$_5$NHCO—(CH$_2$)$_5$NHCO(CH$_2$)$_5$—NHZ | CH$_2$ | 1 | H | C$_{36}$H$_{60}$N$_6$O$_6$ | 672.5 | 673.6 |
| 116 | 4 | —CO(CH$_2$)$_5$NHCO—(CH$_2$)$_5$NHCO(CH$_2$)$_5$—NH$_2$ | CH$_2$ | 1 | H | C$_{28}$H$_{54}$N$_6$O$_4$ | 538.4 | 539.4 |
| 117 | 4 | —CO(CH$_2$)$_3$CO$_2$H | CH$_2$ | 1 | H | C$_{15}$H$_{27}$N$_3$O$_4$ | 313.2 | 314.3 |
| 118 | 4 | —CO(CH$_2$)$_3$CO$_2$Bn | CH$_2$ | 1 | H | C$_{22}$H$_{33}$N$_3$O$_4$ | 403.3 | 404.3 |
| 119 | 4 | —CO(CH$_2$)$_6$NH$_2$ | CH$_2$ | 1 | H | C$_{17}$H$_{34}$N$_4$O$_2$ | 326.3 | 327.3 |
| 120 | 4 | —CO(CH$_2$)$_7$NH$_2$ | CH$_2$ | 1 | H | C$_{18}$H$_{36}$N$_4$O$_2$ | 340.3 | 341.3 |
| 121 | 4 | —CO(CH$_2$)$_{16}$Me | CH$_2$ | 1 | H | C$_{28}$H$_{55}$N$_3$O$_2$ | 465.4 | 466.4 |
| 122 | 4 | —CO(CH$_2$)$_6$—Gua | CH$_2$ | 1 | H | C$_{18}$H$_{36}$N$_6$O$_2$ | 368.3 | 369.3 |
| 123 | 4 | —SO$_2$(CH$_2$)$_7$CH$_3$ | CH$_2$ | 1 | H | C$_{18}$H$_{37}$N$_3$O$_3$S | 375.3 | 376.3 |
| 124 | 4 | —CO(CH$_2$)$_{11}$NH$_2$ | CH$_2$ | 1 | H | C$_{22}$H$_{44}$N$_4$O$_2$ | 396.4 | 397.4 |
| 125 | 4 | —COCH$_2$NHZ | CH$_2$ | 1 | H | C$_{20}$H$_{30}$N$_4$O$_4$ | 390.2 | 391.3 |
| 126 | 4 | —CO(CH$_2$)$_2$NHZ | CH$_2$ | 1 | H | C$_{21}$H$_{32}$N$_4$O$_4$ | 404.2 | 405.3 |
| 127 | 4 | —CO(CH$_2$)$_3$NHZ | CH$_2$ | 1 | H | C$_{22}$H$_{34}$N$_4$O$_4$ | 418.3 | 419.3 |
| 128 | 4 | —CO(CH$_2$)$_2$NH$_2$ | CH$_2$ | 1 | H | C$_{12}$H$_{24}$N$_4$O$_2$ | 256.2 | 257.2 |
| 129 | 4 | —CO(CH$_2$)$_5$NHZ | CH$_2$ | 1 | H | C$_{24}$H$_{38}$N$_4$O$_4$ | 446.3 | 447.4 |
| 130 | 4 | —COCH$_2$—Gua | CH$_2$ | 1 | H | C$_{13}$H$_{26}$N$_6$O$_2$ | 298.2 | 299.3 |
| 131 | 4 | —CO(CH$_2$)$_2$NH$_2$ | CH$_2$ | 1 | H | C$_{13}$H$_{26}$N$_4$O$_2$ | 20.2 | 271.3 |
| 132 | 4 | —CO(CH$_2$)$_2$—Gua | CH$_2$ | 1 | H | C$_{14}$H$_{28}$N$_6$O$_2$ | 312.2 | 313.3 |
| 133 | 4 | —CO(CH$_2$)$_3$—Gua | CH$_2$ | 1 | H | C$_{15}$H$_{30}$N$_6$O$_2$ | 326.3 | 327.3 |
| 134 | 4 | —CO(CH$_2$)$_5$—Gua | CH$_2$ | 1 | H | C$_{17}$H$_{34}$N$_6$O$_2$ | 354.3 | 355.3 |
| 135 | 4 | —CO(CH$_2$)$_6$NH$_2$ | CH$_2$ | 1 | CN | C$_{18}$H$_{33}$N$_5$O$_2$ | 351.3 | 352.4 |
| 136 | 4 | —CO(CH$_2$)$_7$NH$_2$ | CH$_2$ | 1 | CN | C$_{19}$H$_{35}$N$_5$O$_2$ | 365.3 | 366.3 |

TABLE 6

Examples of Group II (iii)

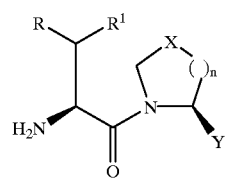

| No. | R | R$^1$ | X | n | Y | Formula | Calculated Mol. Wt. | FAB Mass spec. [M + H]+ |
|---|---|---|---|---|---|---|---|---|
| 137 | H | —OCH$_2$CONH(CH$_2$)$_5$—CO$_2$H | CH$_2$ | 1 | H | C$_{15}$H$_{27}$N$_3$O$_5$ | 329.2 | 330.3 |
| 138 | H | —OCH$_2$CONH(CH$_2$)$_5$—CO$_2$Bn | CH$_2$ | 1 | H | C$_{22}$H$_{33}$N$_3$O$_5$ | 419.3 | 420.3 |
| 139 | H | —OCH$_2$CONH(CH$_2$)$_4$—CO$_2$Bn | CH$_2$ | 1 | H | C$_{21}$H$_{31}$N$_3$O$_5$ | 405.2 | 406.3 |
| 140 | H | —OCH$_2$CONH(CH$_2$)$_4$—CO$_2$H | CH$_2$ | 1 | H | C$_{14}$H$_{25}$N$_3$O$_5$ | 315.2 | 316.3 |
| 141 | CH$_3$ | —OCH$_3$ | CH$_2$ | 1 | H | C$_9$H$_{18}$N$_2$O$_2$ | 186.1 | 187.2 |
| 142 | CH$_3$ | —OC$_2$H$_5$ | CH$_2$ | 1 | H | C$_{10}$H$_{20}$N$_2$O$_2$ | 200.1 | 201.2 |
| 143 | CH$_3$ | —O(CH$_2$)$_5$CH$_3$ | CH$_2$ | 1 | H | C$_{14}$H$_{28}$N$_2$O$_2$ | 256.2 | 257.3 |
| 144 | CH$_3$ | —OCH$_2$CONH(CH$_2$)$_5$—CO$_2$Bn | CH$_2$ | 1 | H | C$_{23}$H$_{35}$N$_3$O$_5$ | 433.3 | 434.3 |
| 145 | CH$_3$ | —OCH$_2$CONH(CH$_2$)$_5$—CO$_2$H | CH$_2$ | 1 | H | C$_{16}$H$_{29}$N$_3$O$_5$ | 343.2 | 344.3 |
| 146 | CH$_3$ | —OCH$_2$CONH(CH$_2$)$_4$—CO$_2$Bn | CH$_2$ | 1 | H | C$_{22}$H$_{33}$N$_3$O$_5$ | 419.2 | 420.3 |
| 147 | CH$_3$ | —OCH$_2$CONH(CH$_2$)$_4$—CO$_2$H | CH$_2$ | 1 | H | C$_{15}$H$_{27}$N$_3$O$_5$ | 329.2 | 330.3 |

TABLE 7

Example of Group III

| No. | Structure | Formula | Calculated Mol. Wt. | FAB Mass spec. [M + H]+ |
|---|---|---|---|---|
| 148 | (structure shown) | $C_{32}H_{54}N_8O_4$ | 614.4 | 615.4 |

TABLE 8

Specific examples of compounds A-B, containing amide bond bioisosteres.

| No. | A-B | Formula | Calculated Mol. Wt. | FAB Mass spec. [M + H]+ |
|---|---|---|---|---|
| 149 | (structure shown) | $C_{11}H_{21}N$ | 167.2 | 168.2 |
| 150 | (structure shown) | $C_{12}H_{20}N_2$ | 192.2 | 193.2 |
| 151 | (structure shown) | $C_{12}H_{20}N_2$ | 192.2 | 193.2 |
| 152 | (structure shown) | $C_{10}H_{20}N_2S$ | 200.1 | 201.2 |

TABLE 9

Selected $K_i$ values against DP-IV.

| No. | $K_i(M)$ |
|---|---|
| 2 | $6.4 \times 10^{-8}$ |
| 7 | $7.6 \times 10^{-6}$ |

TABLE 9-continued

Selected $K_i$ values against DP-IV.

| No. | $K_i(M)$ |
|---|---|
| 11 | $2.2 \times 10^{-9}$ |
| 20 | $1.7 \times 10^{-9}$ |
| 23 | $5.0 \times 10^{-10}$ |
| 35 | $3.7 \times 10^{-8}$ |
| 38 | $9.8 \times 10^{-9}$ |
| 44 | $2.0 \times 10^{-9}$ |
| 59 | $1.5 \times 10^{-7}$ |
| 66 | $1.8 \times 10^{-7}$ |
| 97 | $5.0 \times 10^{-10}$ |
| 110 | $2.5 \times 10^{-7}$ |
| 136 | $1.7 \times 10^{-8}$ |
| 143 | $9.4 \times 10^{-7}$ |
| 150 | $1.7 \times 10^{-6}$ |

Schematic Representations for General Preparation of all Classes of Compounds

Table 1

Compounds can be made by an adaption of the general route described by E. Schön et al., *Biol. Chem. Hoppe-Seyler*, 1991, 372, 305–311.

TABLE 2

(a) R: —CN

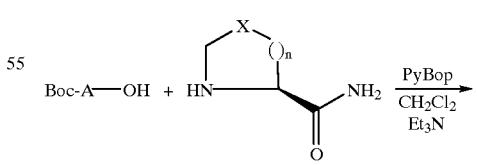

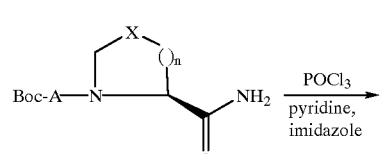

TABLE 2-continued

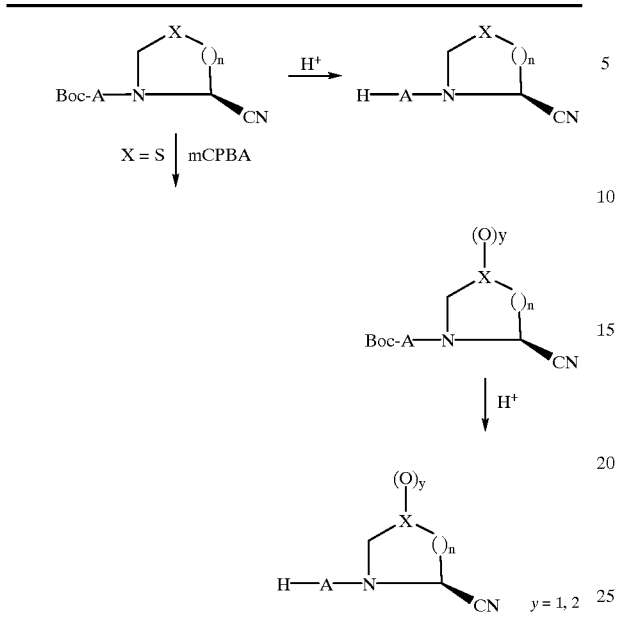

(b) R: —CH=NPh

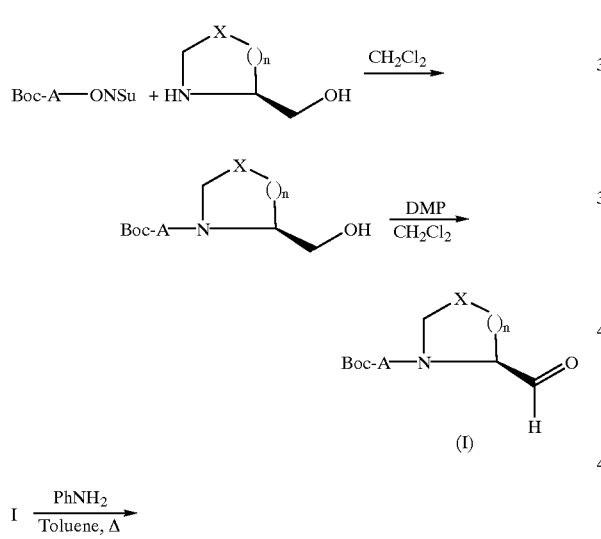

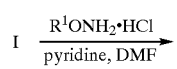

I $\xrightarrow{\text{PhNH}_2}{\text{Toluene, }\Delta}$

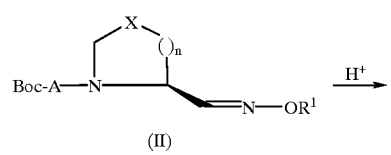

(c) R:

$$\text{CH}=\text{N}^{\text{OR}^1}$$

I $\xrightarrow{R^1ONH_2 \cdot HCl}{\text{pyridine, DMF}}$

TABLE 2-continued

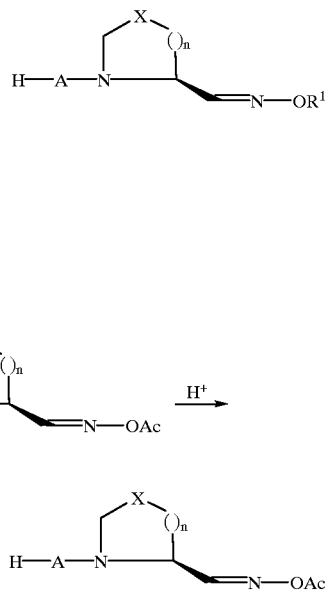

For $R^1$ = —Ac (II) $\xrightarrow{\text{Py, Ac}_2\text{O}}{\text{CH}_2\text{Cl}_2}$

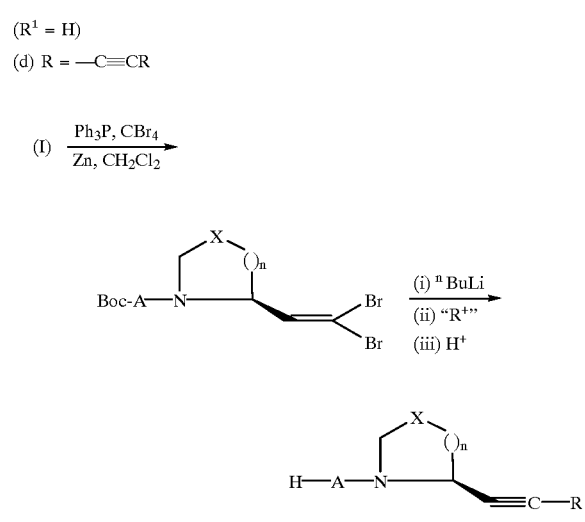

($R^1$ = H)

(d) R = —C≡CR (I) $\xrightarrow{\text{Ph}_3\text{P, CBr}_4}{\text{Zn, CH}_2\text{Cl}_2}$

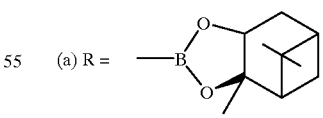

TABLE 3

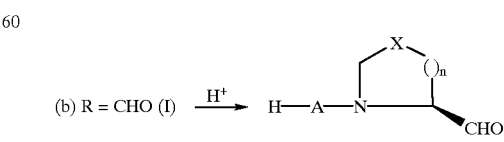

Prepared by method of: W.W. Bachovchin et al., J. Biol. Chem., 1990, 265, 3738–3743.

TABLE 4
(W, P = Protecting groups; P¹, P² = Groups as described in corresponding tables)
(a) R = CN
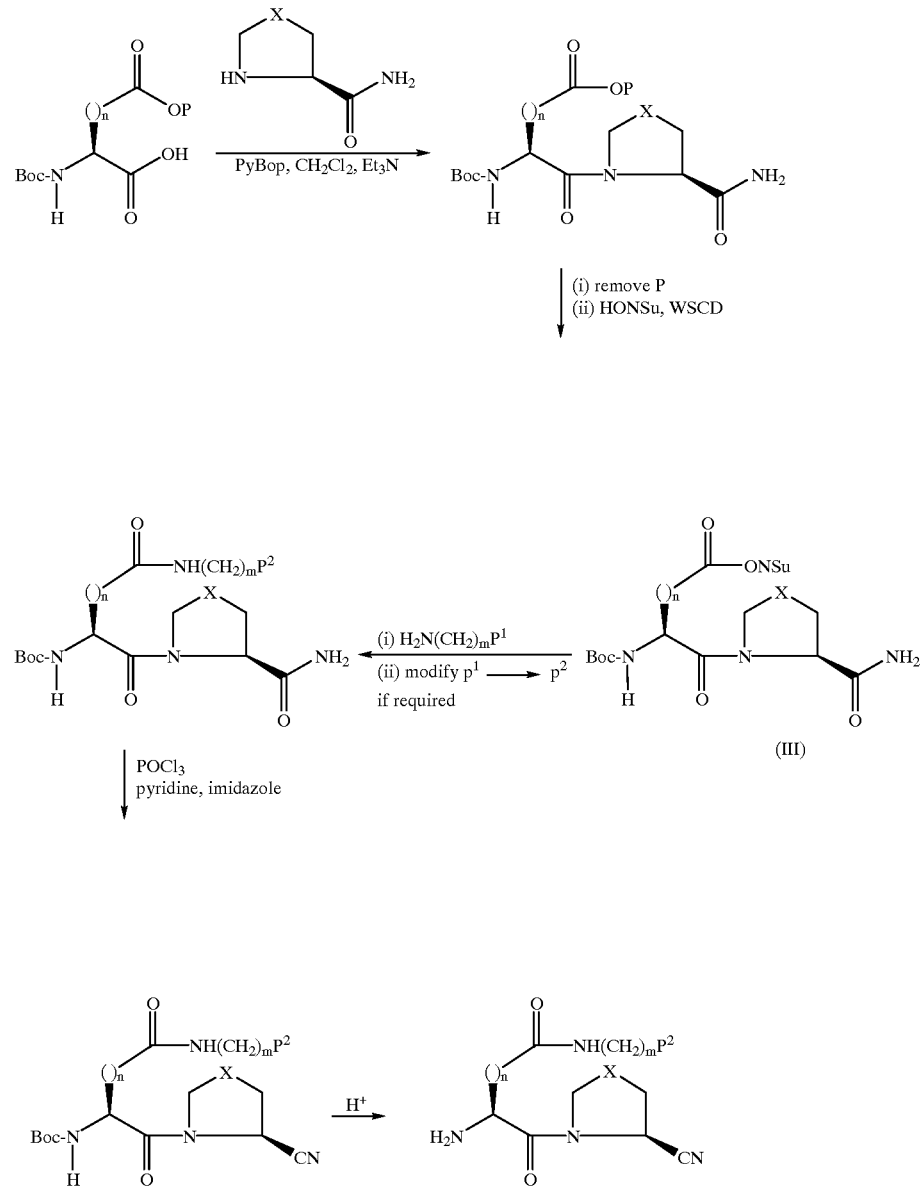

TABLE 4-continued
(W, P = Protecting groups; $P^1$, $P^2$ = Groups as described in corresponding tables)
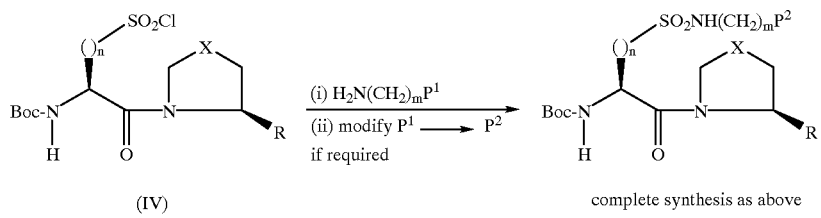
(IV) was prepared via method of G. Luisi et al., *Tet. Lett.*, 1993, 34, 2391–2392.
(c) For R=H, modify above procedure as described for Table 1 examples.
TABLE 5
(a) R = CN
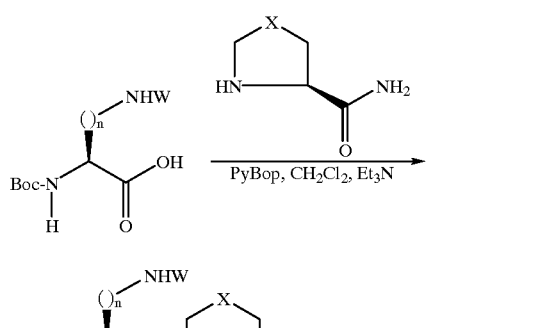
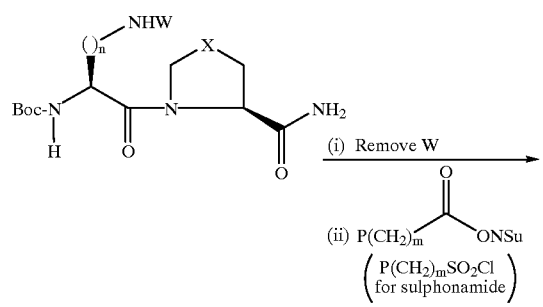
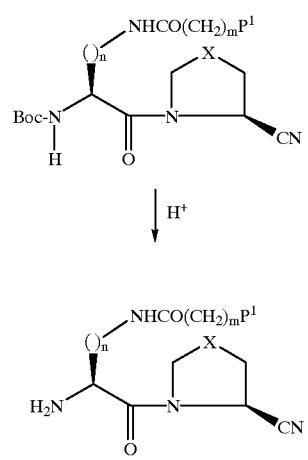
(b) R=H, modify above procedure as described for Table 1 examples.
TABLE 6
Use method described for Table 5 examples for preparation of (VI) from (V)
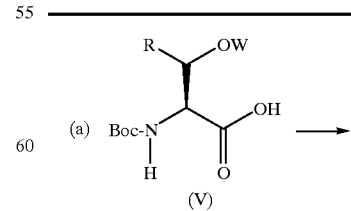
(a)

TABLE 6-continued
Use method described for Table 5 examples for preparation of (VI) from (V)
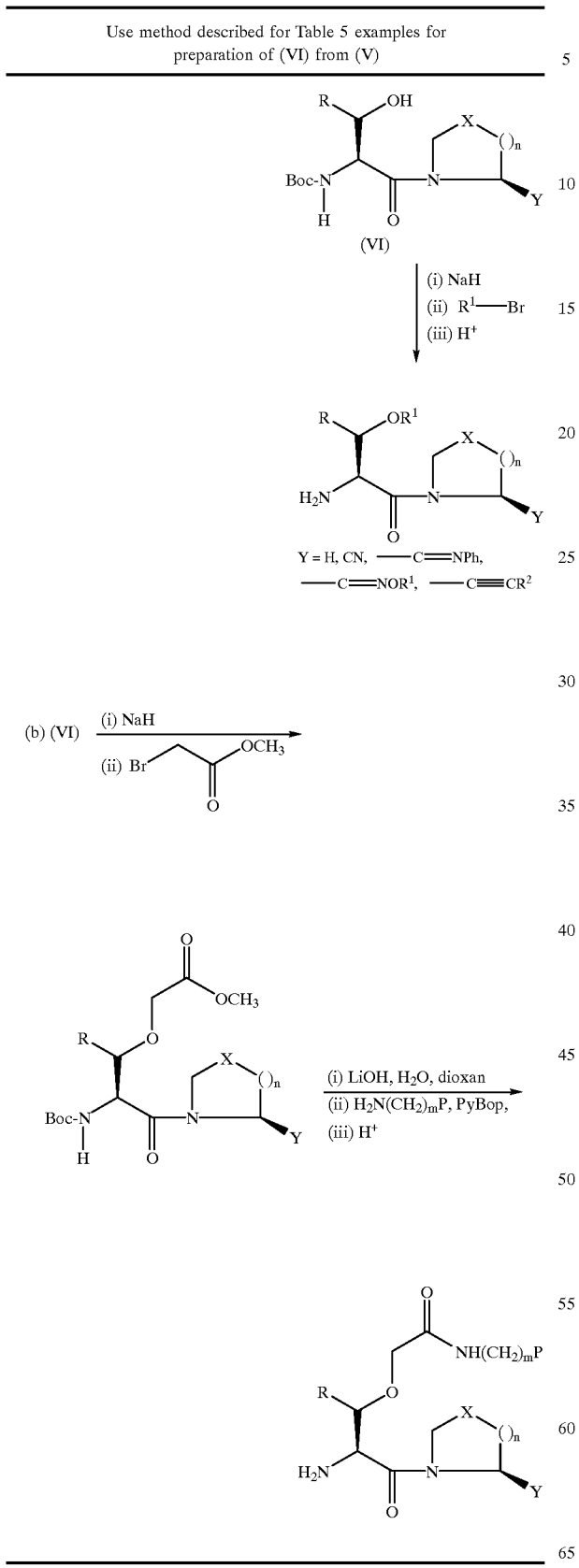
TABLE 7
Standard coupling, dehydration and deprotection sequence similar to above schemes.
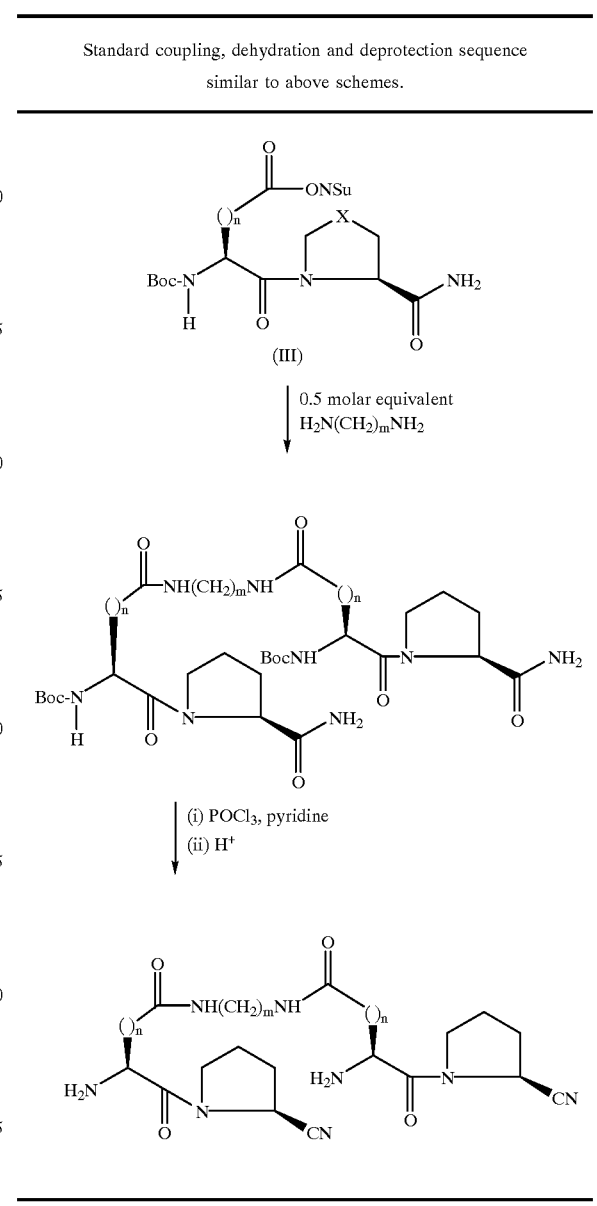
TABLE 8
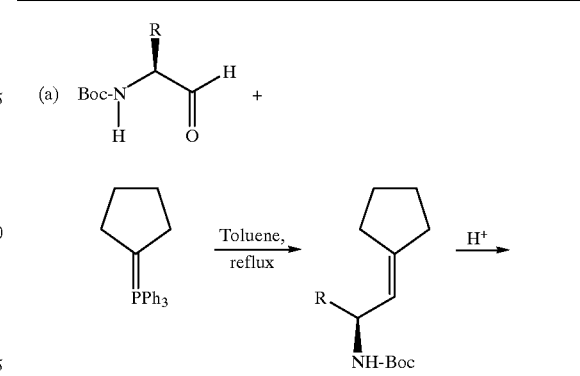

TABLE 8-continued

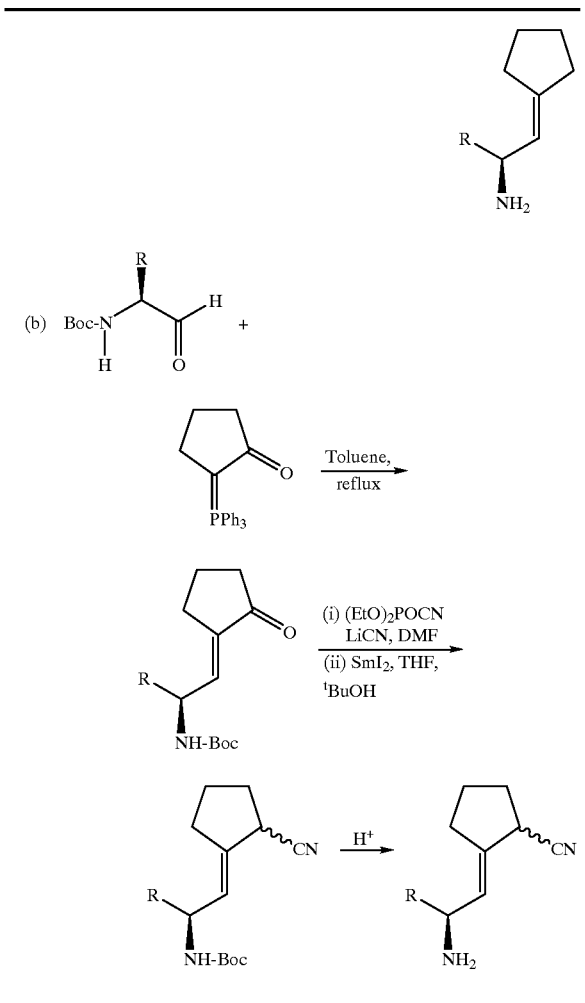

Thioamides were prepared by the method described by K. Clausen et al. *Tetrahedron*, 1981, 37, 3635–3639. Other amide bioisosteres can be prepared from literature precedent (A. F. Spatola in "Chemistry and Biochemistry of Amino Acids, Peptides and Proteins", Vol. III, B. Weinstein Ed., Marcel Dekker, New York, 1983, p. 267).

Experimental Details for Specific Examples

EXAMPLE 1

2-(S)-Cyano-1-isoleucylpyrrolidine (11)

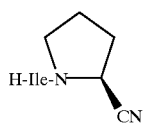

Di-isopropylethylamine was added to a solution of H-ProNH$_2$. HCl (225 mg, 1.50 mmol) in dry CH$_2$Cl$_2$ (15 cm$^3$) until the pH was adjusted to 9. BocIleONSu was added in one portion and the mixture stirred for 16 h, under a nitrogen atmosphere. The solvent was evaporated and the residue treated in the standard way, i.e. the residue was partitioned between ethyl acetate (60 cm$^3$) and 0.3 N KHSO$_4$ solution (10 cm$^3$). The organic layer was further washed with saturated NaCHO$_3$ solution (10 cm$^3$), water (10 cm$^3$) and brine (5 cm$^3$). The solution was dried (Na$_2$SO$_4$) and evaporated at reduced pressure. The crude product was passed down a short plug of silica gel, eluting with hexane-:ethyl acetate, (10:90 to 0:100) to yield 301 mg (92%) of BocIleProNH$_2$ as a colourless foam.

$^1$H NMR (CDCl$_3$), δ (ppm); 6.90 (1H, br.s); 5.51 (1H, br.s); 5.18 (1H, d, J=9.6 Hz); 4.62 (1H, dd, J=2.6, 7.0 Hz); 4.29 (1H, dd, J=8.4, 9.2 Hz); 3.79–3.58 (2H, m); 2.36 (1H, m); 2.09–157 (5H, m); 1.43 (9H, s); 1.17 (1H, m); 0.95 (3H, d, J=6.6 Hz); 0.90 (3H, t, J=7.3 Hz).

Imidazole (84 mg, 1.24 mmol) was added to a solution of BocIleProNH$_2$ in dry pyridine (10 cm$^3$), under a nitrogen atmosphere. The solution was cooled to −35° C., before the dropwise addition of POCl$_3$ (0.25 cm$^3$, 2.48 mmol). The reaction was stirred at −30° C. to −20° C. for 60 min. The solution was then evaporated and the crude residue subjected to column chromatography (silica gel) to yield 180 mg (94%) of 2-(S)-cyano-1-[N-(t-butoxycarbonyl) isoleucyl]pyrrolidine as a colourless oil.

$^1$H NMR (CDCl$_3$), δ (ppm); 5.14 (1H, d, J=92 Hz); 4.80 (1H, dd, J=26, 7.1 Hz); 4.22 (1H, dd, J=7:9, 9.1 Hz); 3.81 (1H, m), 3.71 (1H, m), 2.30-2.12 (4H, m); 1.75 (1H, m); 1.60 (1H, m); 1.42 (9H, s); 1.19 (1H, m); 0.97 (3H, d, J=6.9 Hz); 0.91 (3H, t,J=7.3 Hz).

$^{13}$C NMR (CDCl$_3$), δ (ppm); 171.7, 155.6, 118.0, 79.6, 56.0, 46.5, 46.0, 37.8, 29.6, 28.1, 25.0, 24.2, 15.2, 10.9.

Deprotection was carried out by stirring with trifluoroacetic acid for 60 min. Evaporation and lyophilisation from water afforded 60 mg of 2-(S)cyano-1-isoleucylpyrlidine (11) as a white, fluffy solid.

FAB Mass Spec: Calculated 209.3, Found (M+H)$^+$= 210.2.

$^1$H NMR (D$_2$O), δ (ppm); 4.3 (1H, m); 3.64 (1H, d, J=5.6 Hz); 3.16 (2H, m); 1.86-1.48 (5H, m); 0.98 (1H, m); 0.68 (1H, m); 0.51 (3H, d, J=6.9 Hz); 0.38 (3H, t, J=7.3 Hz).

$^{13}$NMR (D$_2$O), δ (ppm); 169.7, 119.7, 57.3, 48.6, 48.1, 36.9, 30.2, 25.8, 24.5, 15.4, 11.5.

EXAMPLE TWO

H-Glu[NH(CH$_2$)$_7$CONH(CH$_2$)$_3$NHZ]pyrrolidide (64)

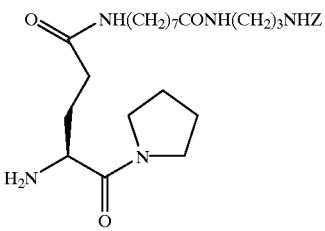

Di-isopropylethylamine was added to a solution of BocGlu(OH)pyrrolidide (193 mg, 0.64 mmol) and PyBop (500 mg, 0.96 mmol) in CH$_2$Cl$_2$ (6 cm$^3$) to adjust the pH of the mixture to 9. After sting for 5 min, a solution of benzyl 8-amino otanoate (220 mg, 0.77 mmol) in CH$_2$Cl$_2$ (5 cm$^3$) was added. The mixture was stirred at room temp for 16 h. The reaction was worked up in the standard procedure as described in example one. The crude residue was subjected to column chromatography (1% to 3% methanol in ethyl acetate) to obtain 344 mg (99%) of BocGlu[NH(CH$_2$)$_7$CO$_2$Bn]pyrrolidide as a colourless solid $^1$H NMR (CDCl$_3$), δ (ppm); 7.35 (5H, s); 6.63 (1H, br.t, J=6.7 Hz); 5.65 (1H, d, J=8.3 Hz); 5.11 (2H, s); 4.36 (1H, dt, J=2.6, 8.9 Hz); 3.55-3.20 (6H, m); 2.34 (2H, t, J=7.3 Hz); 2.26 (2H, dd, J=5.6, 7.3 Hz); 2.11-1.48 (10H, m); 1.43 (9H, s); 1.32-1.27 (6H, m).

Hydrogen gas was bubbled through a solution of BocGlu[NH(CH$_2$)$_7$(CO$_2$Bn]pyrrolidide (230 mg, 0.43 mmol) in ethyl acetate (10 cm$^3$), containing 10% palladium on charcoal (50 mg). After 90 min, the reaction vessel was flushed with nitrogen, the solution filtered through a pad of celite and the solvent evaporated to yield 187 mg (98%) of BocGlu[NH(CH$_2$)$_7$CO$_2$H]pyrrolidide as a colourless oil.

Di-isopropylethylamine was added to a solution of BocGlu[NH(CH$_2$)$_7$CO$_2$H]pyrrolidide (125 mg, 0.28 mmol) and PyBop (221 mg, 0.43 mmol) in CH$_2$Cl$_2$ (10 cm$^3$) to adjust the pH of the solution to 9. After stirring for 5 min, a solution of ZNH(CH$_2$)$_3$NH$_2$. HCl (90 mg, 0.37 mmol) and di-isopropylethylamine (38 mg, 0.37 mmol) was added in one portion. The solution was stirred for 18 h then treated in the standard procedure as described for example one. The crude residue was subjected to column chromatography (2% to 15% methanol in ethyl acetate) to afford 151 mg (85%) of BocGlu[NH(CH$_2$$_7$CONH(CH$_2$)$_3$NHZ]pyrrolidide as a colourless oil.

$^1$H NMR (CDCl$_3$), δ (ppm); 7.35 (5H, s); 6.60 (1H, br.t, J=7.2 Hz); 6.14 (1H, br.t, J=7.2 Hz); 5.63 (1H, d, J=8.3 Hz); 5.39 (1H, br.t, J=5.6 Hz); 5.10 (2H, s); 4.38 (1H, dt, J=2.3, 9.2 Hz); 3.52-3.13 (1OH, m); 2.26 (2H, t, J=6.9 Hz); 2.17 (2H, t, J=7.6 Hz); 1.98-1.48 (12H, m); 1.44 (9H, s); 1.38-123 (6H, m).

A solution of BocGlu[NH(CH$_2$)$_7$CONH(CH$_2$)$_3$NHZ]pyrrolidide (14 mg, 0.022 mmol) in 4N HCl/dioxan was stirred for 45 min. The solvent was evaporated and the residue dissolved in water, filtered and lyophilised to yield 13 mg of H-Glu[NH(CH$_2$)$_7$CONH(CH$_2$)$_3$NHZ]pyrrolidide (64) as a colourless oil.

FAB Mass Spec: Calculated 531.3, Found (M+H)+= 532.3.

EXAMPLE THREE

H-Lys[CO(CH$_2$)NHSO$_2$Pfp]pyrrolidide (110)

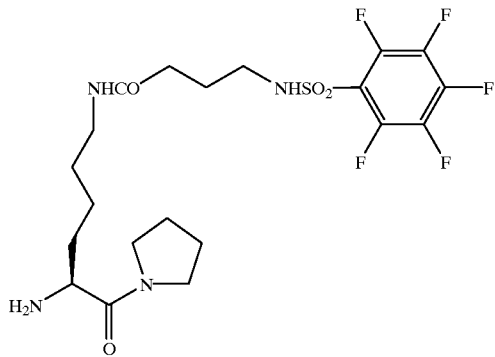

ZNH(CH$_2$)$_3$CO$_2$NSu (570 mg, 1.7 mmol) was added in one portion to a solution of 1-[N-(t-butoxycarbonyl)lysyl] pyrrolidine (745 mg, 2.2 mmol) in dry CH$_2$Ca$_2$. The pH was adjusted to 9 with di-isopropylethylamine and the mixture stirred for 60 min. The solvent was evaporated and the residue treated in the standard procedure as described for example one. Column chromatography (100% ethyl acetate to 15% methanol in ethyl acetate) afforded 620 mg (68%) of BocLys[CO(CH$_2$)$_3$NHZ]pyrrolidide.

$^1$H NMR (CDCl$_3$), δ (ppm); 7.42 (5H, s); 6.31 (1H, br.t, J=6.5 Hz); 5.58 (1H, d, J=8.9 Hz); 5.39 (1H, br.t, J=6.9 Hz); 5.17 (2H, s); 4.44 (1H, m); 3.72-3.20 (8H, m); 2.29 (2H, t, J=7.3 Hz); 2.14-1.83 (8H, m); 1.78-1.41 (4H, m); 1.43 (9H, s).

Hydrogen gas was bubbled through a mixture of BocLys[CO(CH$_2$)$_3$NHZ]pyrrolidide (620 mg, 1.16 mmol) and 10% palladium on charcoal in methanol (10 cm$^3$) containing one molecular equivalent of 2N HCl. After 60 min, the reaction was flushed with nitrogen, and filtered thomugh celite. Evaporation of the solvent afforded 282 mg (49%) of BocLys[CO(CH$_2$)$_3$NH$_2$. HCl]pyrrolidide. This product was dissolved in CH$_2$Cl$_2$ (10 cm$^3$) and stirred, under a nitrogen atmosphere. Di-isopropylethylamine was added to adjust the pH to 9 before the introduction of pentafluorobenzenesulfonyl chloride (45 mg, 0.17 mmol). This mixture was stirred for 16 h. The solvent was evaporated and the crude material treated in the standard procedure described in example one. Column chromatography (100% ethyl acetate to 10% methanol in ethyl acetate) afforded 33 mg (31%) of BocLys[CO(CH$_2$)$_3$NHSO$_2$Pfp]pyrrolidide as a colourless oil.

$^1$H NMR (CDCl$_3$), δ (ppm); 7.19 (1H, br.t, J=6.3 Hz); 6.18 (1H, br.t, J=6.6 Hz); 5.50 (1 d, J=8.4 Hz); 4.38 (1H, m); 3.65-3.16 (8H, m); 2.36 (2, t, J=6.8 Hz); 2.01-1.82 (8H, m); 1.69-1.41 (4H, m); 1.43 (9H, s).

This product was stirred in trifluoroacetic acid (10 cm$^3$) for 30 min. The solvent was evaporated and the residue dissolved in water, filtered and lyophilised to yield 30 mg of H-Lys[CO(CH$_2$)$_3$NHSO$_2$Pfp]Pr1 (110) as a colourless oil.

FAB Mass Spec: Calculated 514.2; Found (M+H)+= 515.2.

EXAMPLE FOUR

H-Thr[(CH$_2$)$_5$CH$_3$]pyrolidide (143)

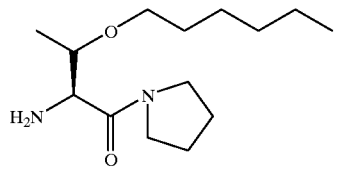

Pyrrolidine (0.88 g, 12.4 mmol) was added to a solution of BocThrONSu (3.0 g, 9.5 mmol) in dry CH$_2$Cl$_2$ (30 cm$^3$), under a nitrogen atmosphere. The reaction was stirred for 60 min at room temperature. The solvent was evaporated and the residue was treated in the standard procedure as described for example one. The residue was subjected to column chromatography (hexane:ethyl acetate, 30:70) to afford 250 g (96%) of 1-[N-(t-butoxycarbonyl)threonyl] pyrrolidine as a colourless oil.

$^1$H NMR (CDCl$_3$), δ (ppm); 5.52 (1H, d, J=6.5 Hz); 4.30 (1H, d, J=7.4 Hz); 4.16 (2H, m); 3.72 (1H, m); 3.46 (3H, w); 1.98-1.82 (4H, m); 1.43 (9H, s); 1.19 (3H, d, J=7.1 Hz).

Sodium hydride (17 mg, 0.70 mmol) was added to a solution of 1-[N-(t-butoxycarbonyl) threonyl]pyrrolidine in dry THF, at 0° C., under a nitrogen atmosphere. The mixture was stirred at 0° C. for 15 min before the introduction of n-hexyl iodide (200 mg, 0.94 mmol). The reaction was then allowed to stir at room temperature for 16 h. The solvent was evaporated and the residue treated in the standard manner as described in example one. The crude product was subjected to column chromatography (hexane:ethyl acetate, 40:60) to afford 25 mg (10%) of BocThr[(CH$_2$)$_5$CH$_3$]pyrrolidide (143).

37

$^1$H NMR (CDCl$_3$), δ (ppm); 5.50 (1H, d, J=6.9 Hz); 4.48 (1Hz m); 3.70-3.32 (7H, m); 1.92-1.80 (6H, m); 1.52 (2H, m); 1.42 (9H, s); 1.30 (6H, m); 1.22 (8H, d, J=6.9 Hz); 0.83 (3H, t, J=7.9 Hz).

BocThr[(CH$_2$)$_5$CH$_3$]pyrrolidide (20 mg, 0.06 mmol) was stirred in 4N HCl/dioxan (5 cm$^3$) for 60 min. The solvent was evaporated, the residue taken up in water, filtered and lyophilised to yield H-Thr[(CH$_2$)$_5$CH$_3$]pyrrolidide (20 mg) as an orange oil. The product was purified by reverse phase HPLC to afford 15 mg of (143) as a colourless oil.

FAB Mass Spec: Calculated 256.2, Found (M+H)$^+$= 257.3.

EXAMPLE FIVE

H-Ile-Ψ[CH═CH]Pyrrolidide (149)

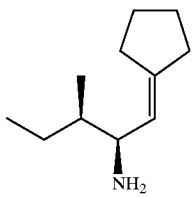

1.6 N "Butyl lithium (0.50 cm$^3$, 0.76 mmol) was added to a stirred solution of cyclopentyl triphenyphosphonium bromide (287 mg, 0.69 mmol) in dry THF (6 cm$^3$), under a nitrogen atmosphere, maintaining the temperature at −30° C. After stirring for 60 min, the solution was further cooled to −50° C. subsequent to the dropwise addition of a solution of N-(t-butoxycarbonyl)-L-isoleucinal (125 mg, 0.58 mmol, prepared by the method of Fehrentz and Castro, *Synthesis*, 1983, 676), in dry THF (4 cm$^3$). After the final addition, the reaction was allowed to slowly attain room temperature, over 3.5 h.

The reaction was quenched with saturated ammonium chloride solution (2 cm$^3$). This was diluted with water (10 cm$^3$) and extracted with diethyl ether (3×20 cm$^3$). The combined ethereal layers were washed with water (10 cm$^3$), dried (Na$_2$SO$_4$) and evaporated to yield 187 mg (>100%) of crude product. Column chromatography (90:10, hexane:Et$_2$O) afforded 53 mg (34%) of Boc-Ile-Ψ[CH═CH]pyirolidide as a colourless oil.

$^1$H NMR (CDCl$_3$), δ (ppm); 0.84 (3H, t, J=6.9 Hz); 0.91 (3H, d, J=7.3 Hz); 1.08 (1H, m); 1.44 (9H, s); 1.48 (1H, m); 1.64 (5H, m); 2.24–2.45 (4H, m); 4.08 (1H, br.s); 4.41 (1H, br.s); 5.12 (1H, dt, J=2.3, 8.9 Hz).

$^{13}$C NMR(CDCl$_3$) δ (ppm); 155.8, 147.4, 119.1, 79.2, 54.8, 40.1, 34.2, 29.6, 28.9, 26.8, 26.6, 26.1, 15.0, 12.1.

Treatment of this product with 4N HCl/dioxan for 35 min removed the Boc-protecting group. The reaction was evaporated, the residue dissolved in water, filtered and lyophilised to yield 24 mg (63%) of H-Ile-Ψ[CH═CH]pyrrolidide (149) as a foamy solid.

FAB Mass Spec: Calculated 167.2, Found (M+H)$^+$= 168.2.

38

EXAMPLES SIX AND SEVEN

H-Ile[(2R)-cyano-Ψ(CH═CH)pyrrolidide] (150)

H-Ile[(2S)-cyano-Ψ(CH═CH)pyrrolidide] (151)

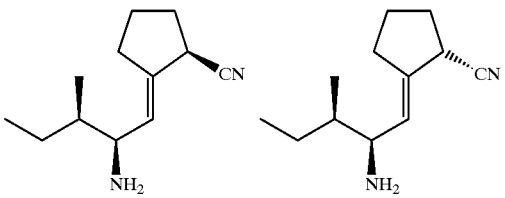

N-(t-Butoxycarbonyl)-L-isoleucinal (2.40 g, 11.2 mmol) and 2-oxy-1-triphenylphosphoranecyclopentane (4.61 g, 13.4 mmol, prepared by method of H. O. House and H. Babed, *J. Org. Chem.*, 1963, 28, 90) were heated, at reflux, in toluene, under a nitrogen atmosphere. After 15 h, the mixture was cooled, and the solvent evaporated. Column chromatography (80:20, hexane:ethyl acetate) of the crude residue afforded 2.33 g (74%) of BocIle-Ψ[CH═CH]pyrrolidin-2-one as a colourless oil.

$^1$H NMR (CDCl$_3$), δ (ppm); 6.29 (1H, dt, J=2.6, 9.2 Hz); 4.59 (1H, br.d); 4.17 (1H, m), 2.82 (1H, m); 2.66-2.50 (2H, m); 2.34 (2H, t, J=7.8 Hz); 1.96 (2H, q, J=7.6 Hz); 1.44 (1H, m); 1.43 (9H, s); 1.12 (1H, m), 0.89 (3H, d, J=5.3 Hz); 0.88 (3H, t, J=6.9 Hz).

Diethylcyanophosponoacetate (0.30 cm$^3$, 1.92 mmol) was added to a solution of BocIle-Ψ[CH═CH]pyrrolidin-2-one (180 mg, 0.64 mmol) and LiCN (0.5 M in DMF, 3.84 cm$^3$, 1.92 mmol) in dry DMF (2 cm$^3$), under a nitrogen atmosphere. The reaction was stirred at room temperature for 30 min. The mixture was diluted with water (20 cm$^3$) and then extracted with ethyl acetate (2×30 cm$^3$). The combined organic layers were washed with water (5×10 cm$^3$), dried (Na$_2$SO$_4$) and evaporated to afford 360 mg (>100%) of crude product A portion of this crude cyano-phosphonate (284 mg, 0.64 mmol) was dissolved in dry THF, and stirred under nitrogen. tert-Butanol (47 mg, 0.64 mmol) was added, followed by the dropwise addition of a solution of samarium (II) iodide (0.1 M in THF, 192 cm$^3$, 1.92 mmol). After the final addition, the reaction was sted for a further 30 min before the addition of 2N HCl (20 cm$^3$). The mixture was extracted with diethyl ether (3×30 cm$^3$). The combined ethereal layers were washed with 10% Na$_2$S$_2$O$_3$ solution (10 cm$^3$), water (2×10 cm$^3$) and brine (2×10 cm$^3$). The solution was dried (Na$_2$SO$_4$), evaporated and the crude residue subjected to column chromatography (90:10, hexane:ethyl acetate) to yield 122 mg (66%) of a diastereomeric mixture of BocIle[2-(RS)-cyano-Ψ(CH═CH)pyrrolidine] as a colourless oil.

$^1$H NMR (CDCl$_3$), δ (ppm); 5.52 (1H, d, J=9.6 Hz); 4.5 (1H, br.s); 4.12 (1H, m); 3.35 (1H, m); 2.57 (1H, m); 2.38 (1H, m); 2.17 (1H, m); 1.91 (2, m); 1.69 (2H, m); 1.53 (1H, m); 1.43 (9H, s); 1.12 (1H, m); 0.92 (1.5 H, d, J=7.3 Hz); 0.91 (1.5 H, d, J=7.3 Hz); 0.89 (15H,d,J=6.6 Hz); 0.86 (1.5H,t,J=6.9 Hz).

Treatment of this diastereomeric mixture with 4N HCl/dioxan for 60 min removed the protecting group. Evaporation of the solvent and subsequent reverse phase HPLC of the residue afforded the two pure diastereomers.

(150), (47 mg, 60%) FAB Mass Spec: Calculated 1922, Found (M+H)$^+$=193.2.

(151), (28 mg, 36%) FAB Mass Spec: Calculated 192.2, Found (M+H)$^+$=193.2.

Preparative methods described herein in relation to Tables 1–8 and in examples one to seven form part of the present invention.

| Abbreviations | |
|---|---|
| Boc | tert-Butyloxycarbonyl |
| Bn | Benzyl |
| BSA | Bovine serum albumin |
| $^n$Bu | n-Butyl |
| Ch | Cyclohexyl |
| DMF | Dimethylformamide |
| DMP | Dess-Martin Periodane |
| EDTA | Ethylenediaminetetraacetic acid |
| FAB | Fast atom bombardment |
| Gua | Guanidinyl |
| HPLC | High performance liquid chromatography |
| $^m$Hx | n-Hexyl |
| Mass Spec | Mass spectrometry |
| mCPBA | meta-Chloroperbenzoic acid |
| Mol Wt | Molecular weight |
| OMSu | N-O-Succinimide |
| Pfp | Pentafluorophenyl |
| Ph | Phenyl |
| Pip | Piperidyl |
| Prl | Pyrrolidide |
| Py | Pyridine |
| PyBop | Benzotriazole-1-yl-oxy-tris-pyrrolidino-phosphonium hexafluorophosphate |
| WSCD | Water soluble carbodiimide |
| Z | Benzyloxycarbonyl |

What is claimed is:

1. An inhibitor of DP-IV mediated processes of general formula:

A—B where B is:

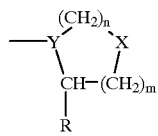

$n=1$ or $2$;
$m=0$, $1$, or $2$;
$X=CH_2$, $O$, $S$, $SO$, $SO_2$, $NH$ or $NR_1$, where $R_1=C_1$–$C_6$ alkyl;
—$Y$=—$N$, —$CH$, or =$C$, provided that when Y is =$C$, the carbonyl group of A is replaced by —$CH$= or —$CF$=;
$R=H$, $CN$, $CHO$, $B(OH)_2$, $C\equiv C$—$R_7$ or $CH=N$—$R_8$, where $R_7=H$, $F$, $C_1$–$C_6$ alkyl, $CN$, $NO_2$, $OR_9$, $CO_2R_9$ or $COR_9$; $R_9=C_1$–$C_6$ alkyl;
$R_8=Ph$, $OH$, $OR_9$, $OCOR_9$ or $OBn$; A is attached to Y; and A is

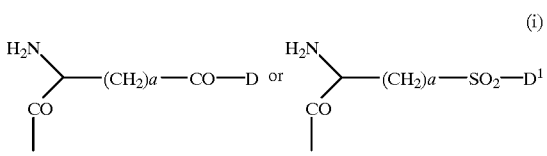

when R is H, CN, C≡C—$R_7$ or CH=N—$R_8$
where $a=1$–$5$; $D$=—$G$—$(CH_2)_b$—$(R_4)_q$—$R_3$; $G=O$, $NH$, $NMe$; $b=0$–$12$; $q=0$–$5$; $D^1$=$D$ with $G\neq O$; $R_4=Z$—$NH$—$(CH_2)_c$— or $NH$—$Z$—$(CH_2)_c$— where $c=1$–$12$ and $Z=CO$, $CH_2$ or $SO_2$; $R_3=CO_2H$ or ester thereof, $CONH_2$, $CONHNH_2$, $CONR_5R_6$, $CONHNR_5R_6$, $PO_3H$ or ester thereof, $SO_3H$, $SO_2NH_2$, $SO_2NR_5R_6$, $OH$, $OR_5$, substituted or unsubstituted aryl or heteroaryl, $NH_2$, $NR_5R_6$, $NHCO_2R_5$, $NHSO_2NR_5R_6$, —$NHCOR_5$, $NH$—$SO_2R_5$, $NH$—$CH(:NR_5R_6)$, $NHCONR_5R_6$, sugar, CO-aminosugar, NHCO-aminosugar or NHCS-aminosugar; and $R_5$ and $R_6$ are independendy selected from H and lower alkyl, fluoroalkyl, and cycloalkyl groups of up to 8 atoms and aryl, heteroaryl and alkyl heteroaryl groups of up to 11 atoms or $R_5$ and $R_6$ may together comprise a chain ($C_3$ to $C_8$);

or A is

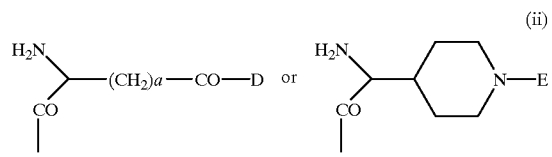

wherein $R^1=H$ or Me, the ring may contain more heteroatoms, $E=J$—$(CH_2)_b$—$(R_4)_q$—$R_3$, $J=CO$, $CH_2$ or $SO_2$, and a, b, q, $R_3$ and $R_4$ are as defined under (i);

or A is

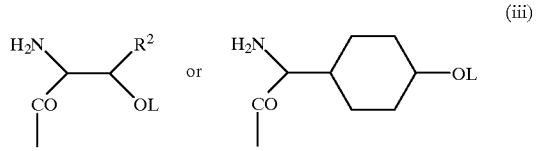

wherein $R_2=H$ or Me, the ring may contain one or more heteroatoms, and $L=(CH_2)_d$—$(CO)$—$(CH_2)_b$—$(R_4)_q$—$R_3$ or $(CH_2)_e$—$NR_1$—$(CH_2)_b$—$(R_4)_q$—$R_3$ where $r=0$ or $1$, $d=0$–$4$, $e=2$–$4$, and b, q, $R_3$ and $R_4$ are as defined under (i);

and wherein at least one $CH_2$ group in a side chain may be replaced by a bioisostere thereof or any amide group which connects A and B or which is in a side-chain of A may be placed by an amide bioisostere.

2. An inhibitor of a DP-IV mediated process according to claim 1 selected from the group consisting of:
N-($N^\omega$-(Benzyloxycarbonylmethyl)asparaginyl)pyrrolidine,
N-($N^\omega$-(Carboxymethyl)asparaginyl)pyrrolidine,
N-($N^\omega$-(3-Carboxypropyl)asparaginyl)pyrrolidine,
N-($N^\omega$-(2-(Benzyloxycarbonyl)ethyl)asparaginyl)pyrrolidine,
N-($N^\omega$-(2-Carboxyethyl)asparaginyl)pyrrolidine,
N-($N^\omega$-(5-(Benzyloxycarbonyl)pentyl)asparaginyl)pyrrolidine,
N-($N^\omega$-(5-Carboxypentyl)asparaginyl)pyrrolidine,
N-($N^\omega$-(3-(Benzyloxycarbonyl)propyl)asparaginyl)pyrrolidine,
N-($N^\omega$-(Benzyloxycarbonylmethyl)glutaminyl)pyrrolidine,
N-($N^\omega$-(Carboxymethyl)glutaminyl)pyrrolidine,
N-($N^\omega$-(2-(Benzyloxycarbonyl)ethyl)glutaminyl)pyrrolidine,
N-($N^\omega$-(3-(Benzyloxycarbonyl)propyl)glutaminyl)pyrrolidine, N-(N^ω-(3-Carboxypropyl)glutaminyl)pyrrolidine,
N-(N^ω-(5-(Benzyloxycarbonyl)pentyl)glutamiyl) pyrrolidine,
N-(N^ω-(5-Carboxypentyl)glutaminyl)pyrrolidine,
N-(N^ω-(2-Carboxyethyl)glutaminyl)pyrrolidine,
N-(N^ω-(7-(Benzyloxycarbonyl)heptyl)glutinyl) pyrrolidine,
N-(N^ω-(7-Carboxyheptyl)glutaminyl)pyrrolidine,
N-(N^ω-(7-(3-(Benzyloxycarbonylamino) propylarninocarbonyl)heptyl)glutamninyl)pyrrolidine,
N-(N^ω-(6-(5-(Benzyloxycarbonyl)penylamocarbonyl) hexyl)glutaminyl)pyrrolidine,
N-(N^ω-(6-(5-Carboxypentylaniiocarbonyl)hexyl) glutaminyl)pyrrolidine,
N-(N^ω-(7-(3-Aminopropylaminocarbonyl)heptyl) glutaminyl)pyrrolidine,
N-(N^ω-(11-(Benzyloxycarbonyl)undecyl)glutaminyl) pyrrolidine,
N-(N^ω-(11-Carboxyundecyl)glutaminyl)pyrrolidine,
N-(N^ω-(6-(Benzyloxycarbonyl)hexyl)glutaminyl) pyrrolidine,
N-(N^ω-(6-Carboxyhexyl)glutaminyl)pyrrolidine,
N-(N^ω-(5-(2,2,2-Trifluoroethylaminocarbonyl)pentyl) glutaminyl)pyrrolidine,
N-(N^ω-(5-(2,2,3,3,4,4,4-Heptafluorobutylaminocarbonyl)pentyl)glutaminyl) pyrrolidine,
N-(N^ω-(5-(6-Hydroxyhexylaminocarbonyl)pentyl) glutaminyl)pyrrolidine,
N-(N^ω-(5-(3-Phenylpropylaminocarbonyl)pentyl) glutaminyl)pyrrolidine,
N-(N^ω-(5-(4-Phenylbutylaminocarbonyl)pentyl) glutaminyl)pyrrolidine,
N-(N^ω-(5-(Dibutylaminocarbonyl)pentyl)glutaminyl) pyrrolidine,
N-(N^ω-(5-(Dihexylaminocarbonyl)pentyl)glutaminyl) pyrrolidine,
N-(N^ω-(5-(Benzylaminocarbonyl)pentyl)glutaminyl) pyrrolidine,
N-(N^ω-(4-(Benzyloxycarbonyl)butyl)glutaminyl) pyrrolidine,
N-(N^ω-(4-Carboxybutyl)glutaminyl)pyrrolidine,
N-(N^ω-(5-(Ethylaminocarbonyl)pentyl)glutaminyl) pyrrolidine,
N-(N^ω-(6-Hydroxyhexyl)glutaminyl)pyrrolidine,
N-(N^ω-(5-(Piperidine-1-carbonyl)pentyl)glutaminyl) pyrrolidine,
N-(N^ω-(5-Carbamoylpentyl)glutaminyl)pyrrolidine,
N-(N^ω-(5-(Decylaninocarbonyl)pentyl)glutaninyl) pyrrolidine,
N-(N^ω-(5-(Heptylaminocarbonyl)pentyl)glutaminyl) pyrrolidine,
N-(N^ω-(5-(Cyclohexylmethylaniinocarbonyl)pentyl) glutaminyl)pyrrolidine,
N-(N^ω-(5-(3-(Benzyloxycarbonylamino) propylaminocarbonyl)pentyl)glutaminyl)pyrrolidine,
N-(N^ω-(5-(3-Aminopropyannocarbonyl)pentyl) glutaminyl)pyrrolidine,
N-(N^ω-(5-(3-Guanidinopropylaminocarbonyl)pentyl) glutaminyl)pyrrolidine,
N-(N^ω-(5-(4-Sulfoxyphenylaminocarbonyl)pentyl) glutaminyl)pyrrolidine,
N-(N^ω-(5-(1-Benzylpiperidin-4-ylaminocarbonyl)pentyl) glutaminyl)pyrrolidine,
N-(N^ω-(5-(Piperidin-4-ylaminocarbonyl)pentyl) glutaminyl)pyrrolidine,
N-(N^ω-(4-(N-Benkvloxycarbonyl-N-(3-benzyloxycarbonylaminopropyl)-aminocarbonyl) butyl)glutaminyl)pyrrolidine,
N-(N^ω-(4-(3-Amiiopropylaminocarbonyl)butyl) glutaminyl)pyrrolidine,
N-(N^ω-(5-(Benzyloxycarbonyl)pentyl)glutaminyl) prolinenitrile,
N-(N^ω-(6-(5-(Benzyloxycarbonyl) pentylamninocarbonyl)hexyl)homoglutaminyl)-pyrrolidine,
N-(N^ω-(6-(5-Carboxypentylaminocarbonyl)hexyl) homoglutaminyl)pyrrolidine,
N-(N^ω-(5-(Benzyloxycarbonyl)pentyl)homoglutaminyl) pyrrolidine,
N-(N^ω-(5-Carboxypentyl)homoglutaminyl)pyrrolidine,
(3S)-3-Amino-N-(5-carboxypentyl)4-oxo4-(1-pyrrolidino)butanesulfonamide,
N-(N^ω-(8-(Glucosaminothiocarbonylamino)octyl) glutninyl)pyrrolidine,
N-((2S)-2-Amino-3-(7-carboxyheptanoylamino) propanoyl)pyrrolidine,
N-((2S)-2-Amino-3-(7-(benzyloxycarbonyl) heptanoylanino)propanoyl)pyrrolidine,
N-(N^ω-(5-Carboxypentanoyl)ornithinyl)pyrrolidine,
N-(N^ω-(5-(Methyloxycarbonyl)pentanoyl)ornithinyl) pyrrolidine,
N-(N^ω-(6-Aminohexanoyl)lysinyl)pyrrolidine,
N-(N^ω-(4-Aminobutanoyl)lysinyl)pyrrolidine,
N-(N^ω-(4-(Pentafluorobenzenesulfonylamino)butanoyl) lysinyl)pyrrolidine,
N-(N^ω-(4-(Pentafluorobenzoylamino)butanoyl)lysinyl) pyrrolidine,
N-(N^ω-(4-(2,2,2-Trifluoroethanesulfonylamino)butanoyl) lysinyl)pyrrolidine,
N-(N^ω-(12-(7-(Benzyloxycarbonylamino) heptanoylamino)dodecanoyl)lysinyl)pyrrolidine,
N-(N^ω-(12-(7-Aminoheptanoylamino)dodecanoyl) lysinyl)pyrrolidine,
N-(N^ω-(6-(6-(6-(Benzyloxycarbonylamino (hexanoylamino)hexanoylamino)hexanoyl)lysinyl) pyrrolidine,
N-(N^ω-(6-(6-(6-Aminohexanoylamino)hexanoylamino) hexanoyl)lysinyl)pyrrolidine,
N-(N^ω-(4-Carboxybutanoyl)lysinyl)pyrrolidine,
N-(N^ω-(4-(Benzyloxycarbonyl)butanoyl)lysinyl) pyrrolidine,
N-(N^ω-(7-Aminoheptanoyl)lysinyl)pyrrolidine,
N-(N^ω-(8-Aminooctanoyl)lysinyl)pyrrolidine,
N-(N^ω-Octadecanoyllysinyl)pyrrolidine,
N-(N^ω-(7-Guanidinoheptanoyl)lysinyl)pyrrolidine,
N-(N^ω-Octanesulfonyllysinyl)pyrroiidine,
N-(N^ω-(12-Aminododecanoyl)lysinyl)pyrrolidine,
N-(N^ω-(2-(Benzyloxycarbonylamino)ethanoyl)lysinyl) pyrrolidine,
N-(N^ω-(3-(Benzyloxycarbonylamino)propanoyl)lysinyl) pyrrolidine,
N-(N^ω-(4(Benzyloxycarbonylamino)butanoyl)lysinyl) pyrrolidine, N-(N^ω-(3-Aminopropanoyl)lysinyl)pyrrolidine,
N-(N^ω-(6-(Benzyloxycarbonylamino)hexanoyl)lysinyl)pyrrolidine,
N-(N^ω-(2-Guanidinoethanoyl)lysinyl)pyrrolidine,
N-(N^ω-(3-Aminopropanoyl)lysinyl)pyrrolidine,
N-(N^ω-(3-Guanidinopropanoyl)lysinyl)pyrrolidine,
N-(N^ω-(4-Guanidinobutanoyl)lysinyl)pyrrolidine,
N-(N^ω-(6-Guanidinohexanoyl)lysinyl)pyrrolidine,
N-(N^ω-(7-Aminoheptanoyl)lysinyl)prolinenitrile,
N-(N^ω-(8Aminooctanoyl)lysinyl)prolinenitrile,
N-(O-(2-(5-Carboxypentylamino)-2-oxoethyl)serinyl)pyrrolidine,
N-(O-(2-(5-(Benzyloxycarbonyl)pentylamino)-2-oxoethyl)serinyl)pyrrolidine,
N-(O-(2-(4-(Benzyloxycarbonyl)butylamino)-2-oxoethyl)serinyl)pyrrolidine,
N-(O-(2-(4-Carboxybutylaiino)-2-oxoetbyl)serinyl)pyrrolidine,
N-(O-Methylthreoninyl)pyrrolidine,
N-(O-Ethylthreoninyl)pyrrolidine,
N-(O-Hexylthreoninyl)pyrrolidine,
N-(O-(2-(5-(Benzyloxycarbonyl)pentylamino)-2-oxoethyl)threoninyl)pyrrolidine,
N-(O-(2-(5-Carboxypentylamino)-2-oxoethyl)threoninyl)pyrrolidine,
N-(O-(2-(4(Benzyloxycarbonyl)butylamino)-2-oxoethyl)threoninyl)pyrrolidine, and
N-(O-(2-(4-Carboxybutylamino)-2-oxoethyl)threoninyl)pyrrolidine.

3. A pharmaceutical composition comprising a DP-IV inhibiting amount of a compound according to claim 1 and a pharmaceutically acceptable carrier.

4. A method of inhibiting DP-IV in a patient, which comprises administering to the patient an amount of a compound according to claim 1 which is effective to inhibit DP-IV.

* * * * *

UNITED STATES PATENT AND TRADEMARK OFFICE
CERTIFICATE OF CORRECTION

PATENT NO.   : 6,201,132 B1
DATED        : March 13, 2001
INVENTOR(S)  : Paul D. Jenkins et al.

It is certified that error appears in the above-identified patent and that said Letters Patent is hereby corrected as shown below:

Column 1,
Line 34, delete "DP-IY" and insert therefor -- DP-IV --.
Line 43, delete "DP-W" and insert therefor -- DP-IV --.

Column 3,
Lines 18 and 34, delete "DP-IY" and insert therefor -- DP-IV --.
Line 35, delete "gp 120" and insert therefor -- gp120 --.
Lines 50-55, delete:

(Group III)"

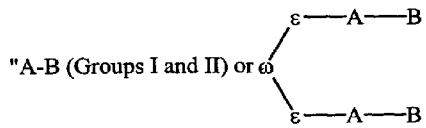

"A-B (Groups I and II) or ω and insert therefor:

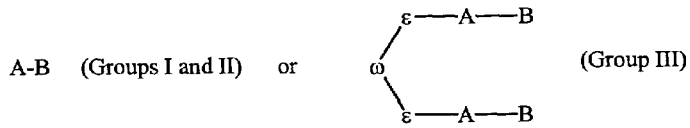

A-B   (Groups I and II)   or      (Group III)

Column 17,
End of Table 3, delete the first occurrence of B* =.
Example 66, delete "-CONH(CH$_{26}$CONH-(CH$_2$)$_5$CO$_2$H" and insert therefor:
-- -CONH(CH$_2$)$_6$CONH-(CH$_2$)$_5$CO$_2$H --.

Column 19,
End of Table 4, delete the first occurrence of G* =.

Column 35,
Line 7, delete "[NH(CH$_2$)$_7$(CO$_2$Bn]" and insert therefor -- [NH(CH$_2$)$_7$CO$_2$Bn] --.
Line 41, delete "H-Lys[CO(CH$_2$)NHSO$_2$Pfp]pyrrolidide(110)" and insert
therefor -- H-Lys[CO(CH$_2$)$_3$NHSO$_2$Pfp]pyrrolidide(110) --.

Column 36,
Line 34, delete "H-Thr[(CH$_{2)5}$CH$_3$]pyrrolidide (143)" and insert therefor
-- H-Thr[(CH$_2$)$_5$CH$_3$]pyrrolidide (143) --.

UNITED STATES PATENT AND TRADEMARK OFFICE
CERTIFICATE OF CORRECTION

PATENT NO. : 6,201,132 B1
DATED : March 13, 2001
INVENTOR(S) : Paul D. Jenkins et al.

It is certified that error appears in the above-identified patent and that said Letters Patent is hereby corrected as shown below:

Column 38,
Line 64, delete "1922" and insert therefor -- 192.2 --.

Column 39,
Line 17, delete "$^{m}$Hx" and insert therefor -- $^{n}$Hx --.

Column 40,
Lines 15-20, delete:

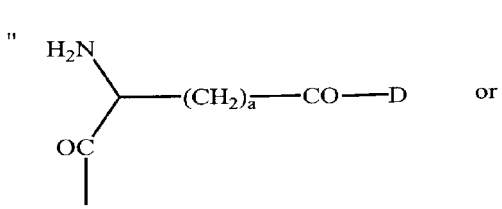 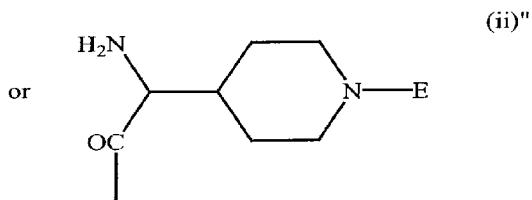

and insert therefor:

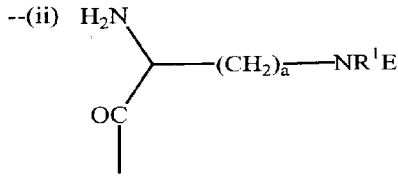 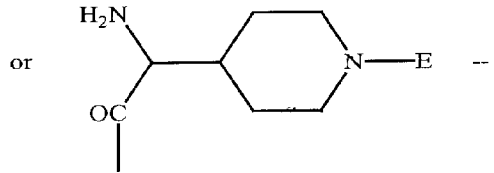

Signed and Sealed this

Twelfth Day of November, 2002

*Attest:*

*Attesting Officer*

JAMES E. ROGAN
*Director of the United States Patent and Trademark Office*